United States Patent
Yun et al.

(10) Patent No.: US 11,382,513 B2
(45) Date of Patent: Jul. 12, 2022

(54) METHODS AND COMPOSITIONS FOR TREATING A CONDITION IN A SUBJECT

(71) Applicant: Palo Alto Investors, Palo Alto, CA (US)

(72) Inventors: Anthony Joonkyoo Yun, Menlo Park, CA (US); Conrad Minkyoo Yun, San Mateo, CA (US)

(73) Assignee: Palo Alto Investors, Palo Alto, CA (US)

( * ) Notice: Subject to any disclaimer, the term of this patent is extended or adjusted under 35 U.S.C. 154(b) by 0 days.

(21) Appl. No.: 15/804,336

(22) Filed: Nov. 6, 2017

(65) Prior Publication Data

US 2018/0125419 A1    May 10, 2018

Related U.S. Application Data

(60) Provisional application No. 62/469,341, filed on Mar. 9, 2017, provisional application No. 62/419,327, filed on Nov. 8, 2016.

(51) Int. Cl.
*A61B 5/00* (2006.01)
*A61N 1/36* (2006.01)
(Continued)

(52) U.S. Cl.
CPC ............. *A61B 5/0036* (2018.08); *A61B 5/24* (2021.01); *A61B 5/4836* (2013.01);
(Continued)

(58) Field of Classification Search
CPC .... A61B 5/4836; A61B 5/4839; A61B 5/4884
See application file for complete search history.

(56) References Cited

U.S. PATENT DOCUMENTS

| 5,707,400 A | 1/1998 | Terry, Jr. et al. |
| 6,086,527 A | 7/2000 | Talpade |

(Continued)

FOREIGN PATENT DOCUMENTS

| JP | 2000-262480 A | 9/2000 |
| KR | 10-131528 B1 | 10/2013 |

(Continued)

OTHER PUBLICATIONS

Kharroubi et al., Diabetes mellitus: The epidemic of the century, World J Diabetes. Jun. 25, 2015; 6(6): 850-867.

(Continued)

*Primary Examiner* — Joseph M Dietrich
(74) *Attorney, Agent, or Firm* — Peter W. Schroen; Bret E. Field; Bozicevic, Field & Francis LLP

(57) ABSTRACT

Methods for treating a condition in a subject, e.g., by enhancing homeostatic capacity of the subject (which may manifest as an increase in a dynamic range of one or more system responses in the subject), are provided. Aspects of embodiments of the methods include: (a) enhancing at least one symptom of the condition to be treated in a manner effective to cause the subject to mount a compensatory response; and (b) diminishing at least one symptom of the condition to be treated; so as to treat the subject for the condition. Also provided are compositions, kits and systems for practicing the subject methods.

13 Claims, 1 Drawing Sheet

(51) Int. Cl.
*A61B 5/24* (2021.01)
*A61B 5/0205* (2006.01)
*A61K 48/00* (2006.01)
*A61K 38/46* (2006.01)

(52) U.S. Cl.
CPC ........ *A61B 5/4884* (2013.01); *A61N 1/36135* (2013.01); *A61B 5/0205* (2013.01); *A61B 5/7275* (2013.01); *A61B 2505/05* (2013.01); *A61K 38/465* (2013.01); *A61K 48/0008* (2013.01)

(56) References Cited

U.S. PATENT DOCUMENTS

| | | |
|---|---|---|
| 6,736,972 B1 | 5/2004 | Matson |
| 6,978,174 B2 | 12/2005 | Gelfand et al. |
| 7,020,521 B1 | 3/2006 | Brewer et al. |
| 7,149,574 B2 | 12/2006 | Yun et al. |
| 7,232,435 B2 | 6/2007 | Hildebrand et al. |
| 7,363,076 B2 | 4/2008 | Yun et al. |
| 7,676,269 B2 | 3/2010 | Yun et al. |
| 7,738,952 B2 | 6/2010 | Yun et al. |
| 7,767,713 B2 | 8/2010 | Yun et al. |
| 7,899,527 B2 | 3/2011 | Yun et al. |
| 7,966,072 B2 | 6/2011 | Yun et al. |
| 8,121,690 B2 | 2/2012 | Yun et al. |
| 8,160,696 B2 | 4/2012 | Bendett et al. |
| 8,247,450 B2 | 8/2012 | Yun et al. |
| 8,457,745 B1 | 6/2013 | Garcia et al. |
| 8,491,459 B2 | 7/2013 | Yun |
| 8,569,277 B2 | 10/2013 | Yun et al. |
| 8,571,650 B2 | 10/2013 | Yun |
| 8,691,877 B2 | 4/2014 | Yun et al. |
| 8,722,016 B2 | 5/2014 | Yun |
| 8,788,041 B2 | 7/2014 | Yun et al. |
| 8,909,340 B2 | 12/2014 | Yun |
| 2001/0053795 A1 | 12/2001 | Bond |
| 2002/0091349 A1 | 7/2002 | Reich |
| 2003/0003165 A1 | 1/2003 | Hong et al. |
| 2003/0097151 A1 | 5/2003 | Smedley et al. |
| 2003/0195427 A1 | 10/2003 | Masakov et al. |
| 2003/0216792 A1 | 11/2003 | Levin et al. |
| 2004/0086576 A1 | 5/2004 | Cianfarani |
| 2004/0230252 A1 | 11/2004 | Kullok et al. |
| 2004/0249416 A1 | 12/2004 | Yun et al. |
| 2005/0015122 A1 | 1/2005 | Mott et al. |
| 2005/0021092 A1 | 1/2005 | Yun et al. |
| 2005/0143788 A1 | 6/2005 | Yun et al. |
| 2005/0153885 A1 | 7/2005 | Yun et al. |
| 2005/0192637 A1 | 9/2005 | Girouard et al. |
| 2005/0192638 A1 | 9/2005 | Gelfand et al. |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0240241 A1 | 10/2005 | Yun et al. |
| 2005/0256028 A1 | 11/2005 | Yun et al. |
| 2005/0267010 A1 | 12/2005 | Goodson et al. |
| 2005/0288721 A1 | 12/2005 | Girouard et al. |
| 2005/0288730 A1 | 12/2005 | Deem et al. |
| 2006/0025821 A1 | 2/2006 | Gelfand et al. |
| 2006/0034847 A1 | 2/2006 | Yun et al. |
| 2006/0035974 A1 | 2/2006 | Yun et al. |
| 2006/0041277 A1 | 2/2006 | Deem et al. |
| 2006/0069012 A1 | 3/2006 | Yun et al. |
| 2006/0116721 A1* | 6/2006 | Yun .................... A61K 31/475 607/2 |
| 2006/0190052 A1 | 8/2006 | Yun et al. |
| 2006/0206149 A1 | 9/2006 | Yun |
| 2006/0216251 A1 | 9/2006 | Morariu |
| 2006/0235474 A1 | 10/2006 | Demarais |
| 2007/0054871 A1 | 3/2007 | Pastore et al. |
| 2007/0112327 A1 | 5/2007 | Yun et al. |
| 2007/0208382 A1* | 9/2007 | Yun .................... A61N 1/36007 607/2 |
| 2008/0075665 A1 | 3/2008 | Yun |
| 2009/0202659 A1 | 8/2009 | Gimble |
| 2010/0119482 A1 | 5/2010 | Yun et al. |
| 2010/0144691 A1 | 6/2010 | Yun et al. |
| 2010/0217358 A1 | 8/2010 | Hebert et al. |
| 2010/0260669 A1 | 10/2010 | Yun et al. |
| 2010/0262220 A1 | 10/2010 | Yun |
| 2010/0280116 A1 | 11/2010 | Yun et al. |
| 2010/0286734 A1 | 11/2010 | Yun et al. |
| 2010/0332443 A1 | 12/2010 | Gartenberg |
| 2011/0015188 A1 | 1/2011 | Yun et al. |
| 2011/0029030 A1 | 2/2011 | Yun et al. |
| 2011/0152967 A1 | 6/2011 | Simon et al. |
| 2011/0256097 A1 | 10/2011 | Yun et al. |
| 2012/0102937 A1 | 5/2012 | Anikhindi et al. |
| 2012/0270876 A1 | 10/2012 | Yun et al. |
| 2013/0053817 A1 | 2/2013 | Yun |
| 2013/0158423 A1 | 6/2013 | Kapoor |
| 2014/0024079 A1 | 1/2014 | Yun |
| 2014/0052211 A1 | 2/2014 | Yun |
| 2014/0065129 A1 | 3/2014 | Yun et al. |
| 2014/0086872 A1 | 3/2014 | Yun et al. |
| 2014/0248217 A1 | 9/2014 | Yun |
| 2014/0303236 A1 | 10/2014 | Van Rooij et al. |
| 2014/0350041 A1 | 11/2014 | Yun et al. |
| 2014/0369969 A1 | 12/2014 | Yun |
| 2015/0015122 A1 | 1/2015 | Koizumi et al. |
| 2015/0025924 A1 | 1/2015 | Yun et al. |
| 2015/0087608 A1 | 3/2015 | Yun |
| 2015/0283265 A1 | 10/2015 | Peyman |
| 2015/0359888 A1 | 12/2015 | Yun |
| 2016/0213296 A1 | 7/2016 | Kikuchi et al. |
| 2016/0375240 A1 | 12/2016 | Yanaki et al. |
| 2018/0362623 A1 | 12/2018 | Tseng et al. |
| 2019/0136232 A1* | 5/2019 | Kellis .................. A61K 31/713 |
| 2019/0282653 A1* | 9/2019 | Knight ................ A61K 31/137 |

FOREIGN PATENT DOCUMENTS

| | | |
|---|---|---|
| WO | WO0197797 A1 | 12/2001 |
| WO | WO2005034871 A2 | 4/2005 |
| WO | WO2005035731 A2 | 4/2005 |

OTHER PUBLICATIONS

Hypothyroidism (underactive thyroid), Symptoms and causes, Mayo Clinic, printed Jan. 2, 2019, 6 pages.
Polycystic ovary syndrome (PCOS), Symptoms and causes, Mayo Clinic, printed Jan. 2, 2019, 3 pages.
Dolson, What is insulin resistance?, Verywell health, updated Sep. 25, 2018, printed Jan. 2, 2019, 4 pages.
Flier, Insulin Receptors and Insulin Resistance, Ann. Rev. Med. 1983, 34:145-60.
Russoniello et al., Heart rate variability and biological age: implications for health and gaming, Cyberpsychol Behav Soc Netw. Apr. 2013;16(4):302-8.
Cameron et al., Venous Plasma Epinephrine Levels and the Symptoms of Stress, Psychosomatic Medicine (1990), 52:411-424.
Compensatory Mechanisms in Heart Failure, Pharamacotherapy, 20(9), 2000, 2 pages.
Freel et al., Mechanisms of Hypertension: The Expanding Role of Aldosterone, J Am Soc Nephrol. Aug. 2004; 15(8): 1993-2001.
Goodman and Gilman's the Pharmacological Basis of Therapeutics, 10th Edition, Chapter 10 Catecholamines, Sympathomimetic Drugs, & Adrenergic Receptor Antagonists, p. 233, published by The McGraw-Hill Companies in 2001.
Greenwood et al., Improvement in insulin secretion in diabetes after diazoxide, Lancet. Feb. 28, 1976;1(7957):444-7.
Pulsatile Drug Delivery Systems: A Review, 4(5): Jun. 2004, 1 page.
Vikram et al., S961, an insulin receptor antagonist causes hyperinsulinemia, insulin-resistance and depletion of energy stores in rats, Biochem Biophys Res Commun. Jul. 23, 2010;398(2):260-5.

(56) References Cited

OTHER PUBLICATIONS

McCraty et al., Heart Rate Variability: New Perspectives on Physiological Mechanisms, Assessment of Self-regulatory Capacity, and Health risk, Glob Adv Health Med Jan. 2015; 4(1): 46-61.

* cited by examiner

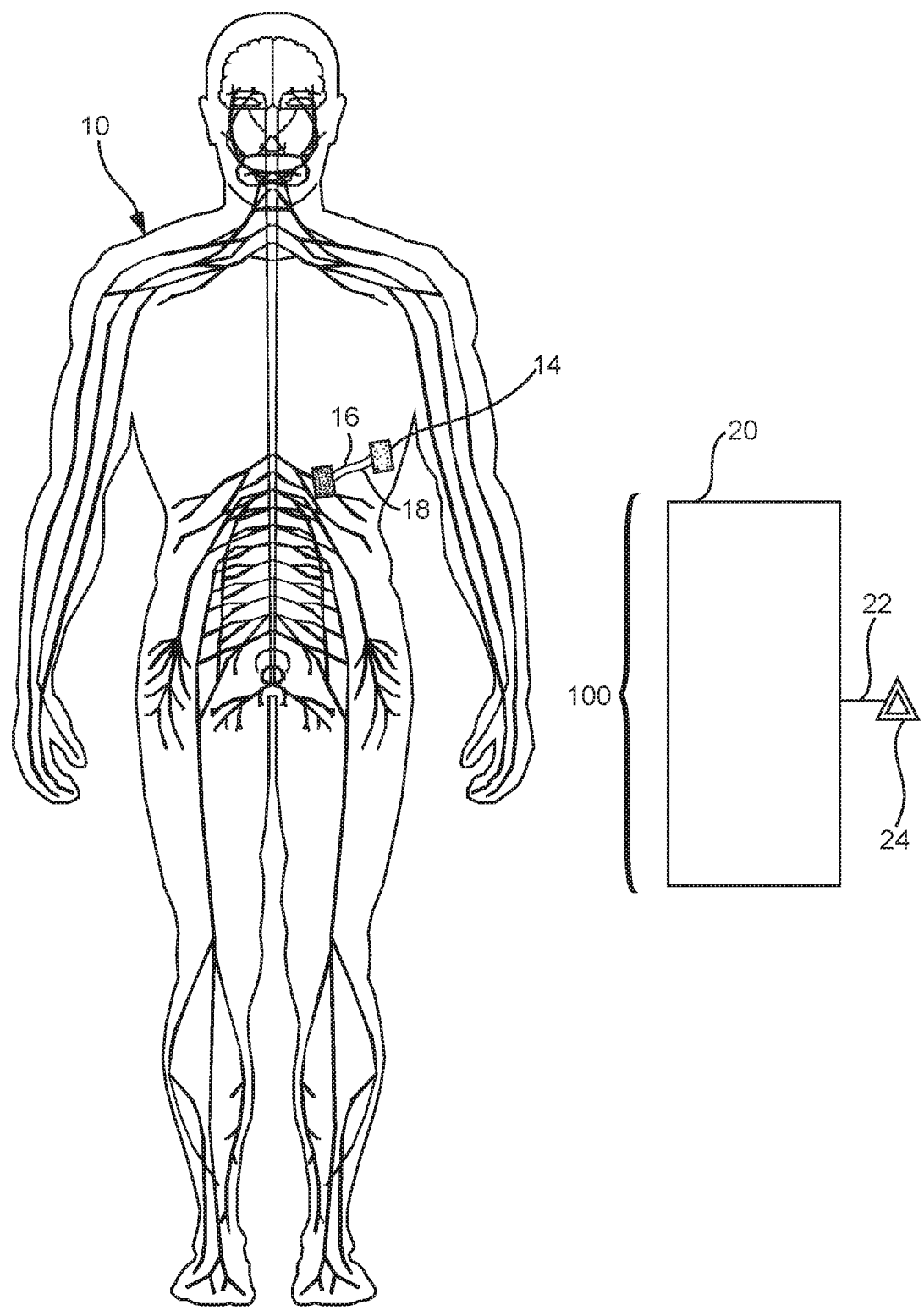

METHODS AND COMPOSITIONS FOR TREATING A CONDITION IN A SUBJECT

CROSS-REFERENCE TO RELATED APPLICATIONS

Pursuant to 35 U.S.C. § 119 (e), this application claims priority to the filing date of: U.S. Provisional Patent Application Ser. No. 62/419,327 filed Nov. 8, 2016 and U.S. Provisional Patent Application Ser. No. 62/469,341 filed on Mar. 9, 2017; the disclosures of which applications are herein incorporated by reference.

INTRODUCTION

Homeostasis refers to the tendency of biological systems to maintain relatively constant conditions in the internal environment while continuously interacting with and adjusting to changes originating within or outside the system. Homeostasis involves continuous motion, adaptation, and change in response to environmental factors. It is through homeostatic mechanisms that body temperature is kept within normal range, the osmotic pressure of the blood and its hydrogen ion concentration (pH) is kept within strict limits, nutrients are supplied to cells as needed, and waste products are removed before they accumulate and reach toxic levels of concentration. These are but a few examples of the thousands of homeostatic control systems within the body. Some of these systems operate within the cell and others operate within an aggregate of cells (organs) to control the complex interrelationships among the various organs.

Homeostatic capacity refers to the capability of systems, such as described above, to self-stabilize in response to stressors. A simple way to visualize homeostatic capacity is to imagine a Weeble™, the popular self-centering children's toy. For organisms, it is life's foundational trait—itself comprised of a hierarchy and network of traits—endowed by nature and shaped by selection. Because the trait is inborn and so pervasively effective, feeling healthy feels like "nothing" when we are young. We become aware of it only after we start losing it midlife. Roller-coaster rides begin to leave us nauseated instead of joyous. We can't tolerate hot or cold weather like before. Sunny days feel too bright and reading menus in low lights becomes more difficult. Recovering from stressors—a late night, hangover, or injury—suddenly take far longer than it used to, if at all. Consider changes that we can't feel. When we are young, homeostatic capacity returns elevated blood glucose and blood pressure to base levels. As homeostatic capacity erodes with age, those levels may no longer self-tune.

SUMMARY

Methods for treating a condition in a subject, e.g., by enhancing homeostatic capacity of the subject (which may manifest as an increase in a dynamic range of one or more system responses in the subject) are provided. Aspects of embodiments of the methods include: (a) enhancing at least one symptom of the condition to be treated, e.g., in a manner effective to cause the subject to mount a compensatory response; and (b) diminishing at least one symptom of the condition to be treated; so as to treat the subject for the condition. Also provided are compositions, kits and systems for practicing the subject methods.

BRIEF DESCRIPTION OF THE FIGURES

FIG. 1 shows an exemplary embodiment of an electric energy applying device operatively positioned in a subject's body in accordance with embodiments of the subject methods.

DETAILED DESCRIPTION

Methods for treating a condition in a subject, e.g., by enhancing homeostatic capacity of the subject (which may manifest as an increase in a dynamic range of one or more system responses in the subject) are provided. Aspects of embodiments of the subject methods include: (a) enhancing at least one symptom of the condition to be treated, e.g., in a manner effective to cause the subject to mount a compensatory response; and (b) diminishing at least one symptom of the condition to be treated; so as to treat the subject for the condition. Also provided are compositions, kits and systems for practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

Aspects of the invention include methods of treating a subject for a condition, such as a disease condition. In the subject methods, at least one symptom of the target condition is enhanced, e.g., in a manner effective to cause the subject to mount a compensatory response, and at least one symptom of the disease condition is diminished, where symptom enhancement and diminishment are performed in a manner effective to treat the condition. By "enhanced" is meant that the magnitude of the symptom is increased. In other words, the target symptom or symptoms is exacerbated. In certain embodiments, the magnitude of enhancement is two-fold or greater, e.g., 5-fold or greater, where in some instances the magnitude is increased by 20-fold or less, such as 10-fold or less. By "diminished" is meant that the magnitude of the symptom is decreased. In other words, the target symptom or symptoms is ameliorated. In certain embodiments, the magnitude of diminishment is two-fold or greater, e.g., 5-fold or greater, up to complete cessation of the symptom, where in some instances the magnitude is decreased by 20-fold or less, such as 10-fold or less.

The term "symptom" is used broadly to refer to any characteristic or sign of the disease condition, i.e., parameter, where symptoms may be any of a number of different types of parameters, including, but not limited to: sympathovagal ratio, high blood pressure, shortness of breath, variations from normal of one or more blood analytes, depression, sleeplessness, and the like. Representative parameters of interest and ranges that can be employed as reference values are provided in Table 1, below:

TABLE 1

| Parameter | Test | Normal Range of Values | Range of Interest |
|---|---|---|---|
| pulmonary gas | Alveolar oxygen | 650-713 mmHg | 600-713 mmHg |
| serum blood gas | pH | 7.35-7.45 | 7.1 to 7.7 |
| | arterial pO2 | 80-100 mmHg | 50-110 |
| | arterial pCO2 | 35-45 mmHg | 10 to 80 |
| | arterial bicarb | 25-35 meq/L | 10 to 40 |
| | alveolar/oxygen ratio | 0.8 | 1 to 0.6 |
| | aa gradient | 10-15 mmHg | 5 to 120 |
| | venous oxygen sat | 60% | 30-80% |
| cardiopulmonary | cardiac output | 3.5 to 5.5 L/min | 1 to 6 |
| | cardiac index | 2.8-3.2 L/min/m2 | 0.5 to 6 |
| | right atrial pressure | 1-7 mmHg | 1 to 30 |
| | right ventricular systolic pressure | 15-25 mmHg | 5 to 50 |
| | right ventricular diastolic pressure | 0-8 mm Hg | 1 to 50 |
| | pulmonary arterial systolic pressure | 15-25 mmHg | 5 to 50 |
| | pulmonary arterial diastolic pressure | 8-15 mmHg | 1 to 30 |
| | mean pulmonary arterial pressure | 10-20 mmHg | 5 to 50 |
| | pulmonary capillary wedge pressure | 6-12 mmHg | 1 to 20 |
| pulmonary function test | tidal volume | 8-15 ml/Kg | 2-20 or 20-80% |
| | total lung capacity | 5-7 liters | 3 to 10 or 20-120% |
| | residual volume | 1.5 to 2.5 liters | 0.5 5 or 20-120% |
| | forced expiratory volume in 1 second | 3.5-4 liters | 0.5 to 6 or 20-120% |
| | functional vital capacity | 4-6 liters | 0.5 to 6 or 20-120% |
| | FEV1/FVC ratio | >75% | 20-120% |
| | forced expiratory flow | 75-125% | 50 to 150% |
| | peak expiratory flow rate | 80-100% | 60-120% |
| | forced expiratory time | <5 seconds | 0-20 seconds |
| | corrected diffusion capacity | 75-80% | 60-140% |
| | corrected QT interval | <440 | <600 |
| sleep study | sleep latency | >10 min | 0-1 hour |
| | total sleep time | >5.5 hours | 0-12 hours |
| | percent rem | >15% of TST | 0-40% total sleep time |
| | percent stage 3-4 non rem | >25% of TST | 0-50% total sleep time |
| | respiratory arousal index | <5/hour total sleep time | 0-40/hour total sleep time |
| | periodic leg movements | <1/hour total sleep time | 0-40/hour total sleep time |
| | apnea index | <1/hour total sleep time | 0-20/hour total sleep time |
| | hypopnea index | <3/hour total sleep time | 0-40/hour total sleep time |

TABLE 1-continued

| Parameter | Test | Normal Range of Values | Range of Interest |
|---|---|---|---|
| | nadir oxygen saturation | >92% | 40-100% |
| | mean oxygen saturation | >95% | 40-100% |
| | desaturation index | <5 defined as >4% for 5 seconds/hour of total sleep time | 0-40 defined as >4% for 5 seconds/hour of total sleep time |
| | highest carbon dioxide | 52 mm Hg | 10-80 mmHg |
| | carbon dioxide >45 mmHg | <20% of total sleep time | 0-60% of total sleep time |
| Serum Markers | Catecholamine levels | | |
| | Acetycholine levels | 650-1500 IU/L | 300-2000 IU/L |
| | Aldosterone levels | 17-70 nmol/day | 5-150 nmol/L/day |
| | Renin levels | 7-76 uU/mL | 3-200 uU/ml |
| | Vasopressin levels | 2-8 pg/mL | 1-20 pg/ml |
| | angiotensin converting enzyme levels | 25-100 IU/L | 5-200 U/L |
| | interleukin 1-3 and 5-13 and 18 | modulate | |
| | Interleukin 4 | decrease | |
| | interferon alpha and beta | modulate | |
| | interferon gamma | increase | |
| | tumor necrosis factor alpha | modulate | |
| | transforming growth factor | modulate | |
| | hemoglobin A1C | 4-8% | 2-12% |
| | Fasting glucose | 3.5-6.0 mmol/L | 1-10 mmol/L |
| | high density lipoprotein | 45-60 | 10 to 90 |
| | low density lipoprotein | 95-130 | 60-200 |
| | triglyceride | <2 mmol/L | 4 to 4 mmol/L |
| | beta natriuretic peptide | 20-40 pg/mL | 0-100 pg/mL |
| | alpha natriuretic peptide | 20-40 pg/mL | 0-50 pg/mL |
| | erythrocyte sedimentation rate | 0-35 mm/Hour | 1-200 mm/Hour |
| | c reactive peptide | <10 mg/L | 1-80 mg/L |
| | transferrin | 1.75 to 3.13 g/L | 0.5 to 6 g/L |
| | Hemoglobin | 135-160 gm/L | 25 to 300 gm/L |
| | hematocrit | 37-54% | 25-60% |
| | ferritin | 20-240 ug/L | 5 to 600 ug/L |
| | iron | 10-40 umol/L | 5 to 100 umol/L |
| | cholinesterase | 650-1500 IU/L | 200-2500 IU/L |
| | Urine adrenaline | 0-80 nmol/day | 0-200 nmol/day |
| | Urine noradrenaline | 0-780 nmol/day | 0-1600 nmol/day |
| | Urine dopamine | 0-3500 nmol/day | 0-7000 nmol/day |
| | adrenocorticotrophic hormone | <19 pmol/L | 0 to 40 pmol/L |
| | antidiuretic hormone | 2-8 pg/mL | 1-20 pg/mL |
| | thrombin clotting time | 10-20 secs | 5-30 secs |
| | total serum cholesterol | 110-120 | 100-300 |
| Additional | body mass index | 20-30 | <40 |
| | systolic blood pressure | <125 | 90-180 |
| | diastolic blood pressure | <75 | 30-100 |
| | pulse pressure | <20 | 20-40 |
| | heart rate | 60-100 | 30-200 |
| | heart rate variability | increase | |
| | respiratory sinus arrhythmia | increase | |

In embodiments of the subject methods, opposing stimuli, e.g., in the form of target symptom enhancement and diminishment stimuli, are administered to the subject. Opposing stimuli are stimuli that have opposing activity, e.g., opposing physiological activity, such that upon administration to a living subject opposing physiological activity is observed, e.g., receptor agonism and antagonism, nerve stimulation and blockage, etc.

In some instances, the target symptom(s) is enhanced by applying an appropriate symptom enhancement stimulus to the subject, where the symptom enhancement stimulus is of a nature and magnitude sufficient to achieve the desired enhancement. In certain embodiments, the applied symptom enhancement stimulus is one of short duration, where by short duration is meant that the applied symptom enhancement stimulus lasts for 1 week or less, e.g., 3 days or less, e.g., 1 day or less, e.g., 12 hours or less, where the duration of the applied symptom enhancement stimulus may be even shorter. Where the symptom enhancement stimulus is a pharmacological stimulus, the duration refers to the period in which the pharmacological agent from an administered dosage is active. Where the symptom enhancement stimulus is an electrical stimulus, the duration refers to the total of electrical applications received by a subject over a given period, analogous to a dose of a pharmacological agent.

Following symptom enhancement via an applied symptom enhancement stimulus, as described above, the symptom enhancement stimulus is removed, e.g., by metabolization of the pharmacological agent or cessation of application of electrical energy, and the subject is permitted to mount a compensatory response. In this following period, no additional symptom enhancement stimulus is administered to the subject. The duration of this period between symptom enhancement stimulus application, which may be referred to as a "holiday" period, may vary, but in some embodiments 1 minute or longer, e.g., 15 minutes or longer, 30 minutes or longer, 45 minutes or longer, 1 hour or longer, 3 hours or longer, 6 hours or longer, 12 hours or longer, 18 hours or longer, 1 day or longer, such 2 days or longer, including 5 days or longer, 10 days or longer, 15 days or longer, where in some instances the holiday period is 30 days or shorter, such as 25 days or shorter, including 20 days or shorter. As such, embodiments of the methods include non-chronic (i.e., non-continuous) application of the symptom enhancement stimulus, e.g., non-chronic administration of a pharmacologic agent. Where desired, symptom diminishment, e.g., as described in greater detail below, may be performed during the holiday period.

In certain embodiments, the methods include close monitoring or supervision of the subject during and/or after application of the symptom enhancement stimulus. This monitoring may be completely automated, or at least in part performed manually, e.g., by a health care professional. For example, a health care professional can closely watch the subject following application of the symptom enhancement stimulus as well as during the holiday period following symptom enhancement stimulus application, and based on this monitoring determine when a next symptom enhancement stimulus should be applied. Monitoring also assures that the symptom enhancement is not so severe as to be ultimately damaging to the subject at an unacceptable level. Certain aspects of the monitoring may be automated. For example, following administration, the subject may enter one or more physiological parameters into an automated system, which uses the input parameters to automatically determine whether the subject is staying within a predetermined set of physiological parameters, or whether intervention is necessary. In certain embodiments, the automated monitoring system may also be integrated with a symptom enhancement stimulus application device, such that the system, based on monitored parameters, determines when next to administer a symptom enhancement stimulus, the duration of the next stimulus, etc. As such, the method may be characterized as applying a first stimulus to the subject and monitoring the subject for a response thereto. Following this first step, the method further includes applying at least a second symptom enhancement stimulus to the subject, wherein the second symptom enhancement stimulus is determined based on the monitored response to the first symptom enhancement stimulus.

In certain embodiments, application of symptom enhancement stimulus to the subject is done in an "irregularly irregular" manner. As such, duration of the symptom enhancement stimulus application events, as well as duration of holiday periods between such events, varies randomly over the entire course of a treatment, or at least a portion thereof. In addition, the variation does not follow any pattern, but instead is random.

In practicing the subject methods, the applied symptom enhancement stimulus may vary, where in some embodiments the symptom enhancement stimulus may be a pharmacological symptom enhancement stimulus and/or an electrical symptom enhancement stimulus. As such, in certain embodiments, the symptom enhancement stimulus is a pharmacological symptom enhancement stimulus. In other embodiments, the symptom enhancement stimulus is an electrical symptom enhancement stimulus. In yet other embodiments, the symptom enhancement stimulus is a combination of pharmacological and electrical symptom enhancement stimuli. Accordingly, in certain embodiments, the symptom enhancement is achieved by administering a pharmacological agent to the subject. In yet other embodiments, the symptom enhancement is achieved by electrical stimulation, e.g., by employing an implanted electrical energy application device. Further details regarding embodiments of pharmacological and electrical stimuli finding use in methods of the invention are provided below.

As summarized above, in addition to enhancing one or more symptoms of a disease condition, aspects of the methods further include diminishing one or more symptoms at some point, e.g., one or more times, during the treatment methods. The symptom(s) which is diminished may be the same or different as the symptom which is enhanced, e.g., as described above. As such, in some embodiments, the methods include a step of diminishing the same symptom or symptoms that was enhanced. In yet other embodiments, the methods include a step of diminishing a different symptom or symptoms from that symptom which was enhanced.

In practicing the subject methods, a target symptom(s) is diminished by applying an appropriate symptom diminishment stimulus to the subject, where the symptom diminishment stimulus is of a nature and magnitude sufficient to achieve the desired symptom diminishment. In certain embodiments, the applied symptom diminishment stimulus is one of short duration, where by short duration is meant that the applied symptom diminishment stimulus lasts for 1 week or less, e.g., 3 days or less, e.g., 1 day or less, e.g., 12 hours or less, 6 hours or less, 3 hours or less, 1 hour or less, 30 minutes or less, 15 minutes or less, 5 minutes or less, 1 minute or less, 30 seconds or less, where the duration of the applied symptom diminishment stimulus may be even shorter. Where the symptom diminishment is a pharmacological stimulus, the duration refers to the period in which the pharmacological agent from an administered dosage is active. Where the symptom diminishment stimulus is an electrical stimulus, the duration refers to the total of electrical applications received by a subject over a given period, analogous to a dose of a pharmacological agent.

Following symptom diminishment via an applied symptom diminishment stimulus, as described above, the symptom diminishment stimulus is removed, e.g., by metabolization of the pharmacological agent or cessation of application of electrical energy. In this following period, no additional symptom diminishment stimulus is administered to the subject. The duration of this period between symptom diminishment stimulus application may vary, but in some embodiments is 1 minute or longer, e.g., 15 minutes or longer, 30 minutes or longer, 45 minutes or longer, 1 hour or longer, 3 hours or longer, 6 hours or longer, 12 hours or longer, 18 hours or longer, 1 day or longer, such 2 days or longer, including 5 days or longer, 10 days or longer, 15 days or longer, where in some instances the holiday period is 30 days or shorter, such as 25 days or shorter, including 20 days or shorter. As such, embodiments of the methods include non-chronic (i.e., non-continuous) application of the symptom diminishment stimulus, e.g., non-chronic administration of a pharmacologic agent. Where desired, symptom enhancement, e.g., as described in greater detail above, may be performed during this symptom diminishment holiday period.

In certain embodiments, application of the symptom diminishment stimulus to the subject is done in an "irregularly irregular" manner. As such, duration of the symptom diminishment stimulus application events, as well as duration of intervening periods between such events, varies randomly over the entire course of a treatment, or at least a portion thereof. In addition, the variation does not follow any pattern, but instead is random.

In practicing the subject methods, the applied symptom diminishment stimulus may vary, where in some embodiments the symptom diminishment stimulus may be a pharmacological symptom diminishment stimulus and/or an electrical symptom diminishment stimulus. As such, in certain embodiments, the symptom diminishment stimulus is a pharmacological symptom diminishment stimulus. In other representative embodiments, the symptom diminishment stimulus is an electrical symptom diminishment stimulus. In yet other embodiments, the symptom diminishment stimulus is a combination of pharmacological and electrical symptom diminishment stimuli. Accordingly, in certain embodiments, the symptom diminishment is by administering a pharmacological agent to the subject. In yet other embodiments, the symptom diminishment is by electrical stimulation, e.g., by employing an implanted electrical energy application device. Further details regarding embodiments of pharmacological and electrical stimuli finding use in methods of the invention are provided below.

In certain embodiments, the methods include close monitoring or supervision of the subject during and/or after application of the symptom diminishment stimulus. This monitoring may be completely automated, or at least in part performed manually, e.g., by a health care professional. For example, a health care professional can closely watch the subject following application of the symptom diminishment stimulus as well as during the holiday period following symptom diminishment stimulus application, and based on this monitoring determine when a next symptom diminishment stimulus should be applied. In certain embodiments, the automated monitoring system may also be integrated with a symptom diminishment stimulus application device, such that the system, based on monitored parameters, determines when next to administer a symptom diminishment stimulus, the duration of the next stimulus, etc. As such, the method may be characterized as applying a first stimulus to the subject and monitoring the subject for a response thereto. Following this first step, the method further includes applying at least a second symptom diminishment stimulus to the subject, wherein the second symptom diminishment stimulus is determined based on the monitored response to the first symptom enhancement stimulus.

As reviewed above, methods of the invention include at least one instance of symptom enhancement and at least one instance of symptom diminishment, e.g., via application of opposing stimuli, such as physiological stimuli, to the subject. In some instances the methods may include a plurality of symptom enhancement events and/or a plurality of symptom diminishment events. The application of symptom enhancement and diminishment events in a given treatment method or protocol, i.e., regimen, may vary, and may be regular, e.g., alternating, or irregular, as desired.

As summarized above, the stimuli that are applied to a subject in practicing methods of the invention may be pharmacological and/or electrical stimuli. As such, embodiments of the invention include administering opposing pharmacological agents to a subject. In other instances, opposing electrical stimuli are administered to a subject.

Administering a Pharmacological Agent

In certain embodiments, the subject invention includes administering an effective amount of a pharmacological agent(s) to a subject, e.g., opposing pharmacological stimuli, such as a symptom enhancing pharmacological agent stimulus and symptom diminishing pharmacological agent stimulus. Any suitable pharmacological agents may be administered, where the pharmaceutical agents may vary depending on whether they are employed as symptom enhancement agents or symptom diminishing agents. That is, embodiments of the subject methods include administering an effective amount, i.e., a therapeutically effective amount, of one or more pharmacological agents to a subject. By "effective amount" is meant a dosage sufficient to cause the subject to mount a compensatory response effective to treat the subject, as desired. The effective amount will vary with the age and physical condition of the subject, severity of the condition being treated, the duration of the treatment, the nature of any concurrent treatment, the pharmaceutically acceptable carrier used if any, and analogous factors within the knowledge and expertise of those skilled in the art.

In certain embodiments, more than one type of agent may be administered at the same or different times to treat the same or different condition. The effective amount of a given agent may vary somewhat from subject to subject, and may depend upon factors such as, but not limited to, the age and condition of the subject, the form of the agent, the route and method of delivery, etc., as noted above. Dosages may be determined in accordance with routine pharmacological procedures known to those skilled in the art. Specific pharmacological agents that may find use in certain embodiments of the subject invention include both pro parasympathetic and pro sympathetic agents.

Pro parasympathetic agents of interest include, but are not limited to: Beta Blockers, e.g., atenolol (Tenormin R), betaxolol (Kerlone R), bisoprolol (Zebeta R), carvedilol (Coreg R), esmolol (Brevibloc R), labetalol (Normodyne R), metoprolol (Lopressor R), nadolol (Corgard R), pindolol (Visken R), propranolol (Inderal R), sotalol (Betapace R), timolol (Blocadren R); Aldosterone Antagonists, e.g., Spironolactone, eplerenone, Angiotensin II Receptor Blockade, candesartan (Atacand R), irbesartan (Avapro R), losartan (Cozaar R), telmisartan (Micardis R) valsartan (Diovan R), eprosartan mesylate (Teveten); ACE inhibitors, e.g., Benazepril (Lotensin R), Captopril (Capoten R), Enalapril (Vasotec R), Fosinopril (Monopril R), Lisinopril (Prinivil R), Moexipril (Univasc R), Quinapril (Accupril R), Ramipril (Altace R), Trandolapril (Mavik R); Statins, e.g., atorvastatin (Lipitor R), cerivastatin (Baycol R), fluvastatin (Lescol R), lovastatin (Mevacor R), pravastatin (Pravachol R), mvastatin (Zocor R); Triglyceride Lowering Agents, e.g., fenofibrate (Tricor R), gemfibrozil (Lopid R), Niacin; Diabetes Agents, e.g., acarbose (Precose R), glimepiride (Amaryl R), glyburide (Micronase R, Diabeta R), metformin (Glucophage R), Miglitol (Glycet R), pioglitazone (Actos R), repaglinide (Prandin R), rosiglitazone (Avandia R); Immunomodulators, e.g., Interferon Alfa-2A (Roferon-A), Interferon Alfa-2b (Intron-A), Interferon Alfa-2b and Ribavirin combo Pack (Rebetron), Interferon Alfa-N3 (Alferon N), Interferon Beta-1A (Avonex), Interferon Beta-1B (Betaseron), Interferon Gamma; agents that binds/reacts to CD4, gp39, B7, CD19, CD20, CD22, CD401, CD40, CD40L and CD23 antigens, rituximab, Nicotine; Sympathomimetics, e.g., trimethaphan, Clonidine, Reserpine, Guanethidine; Antihistamines, e.g., Benadryl, Diphenhydramine, Actifed (Triprolidine), PBZ (Tripelenamine), Allegra (Fexofenadine), Periactin (Cyproheptadine), Antivert or Bonine (Meclizine), Phenergan (Promethazine), Astelin (dispensed as a Nose Spray), Polyhistine (Phenyltoloxamine), Atarax (Hydroxyzine), Seldane (Terfenadine), Benadryl (Diphenhydramine), Semprex (Acrivastine), Bromfed (Brompheneramine), Tavist (Clemastine), Chlortrimeton (Chlorpheniramine), unisom (Doxylamine), Claritin (Loratidine), Zyrtec (Cetirizine), Dramamine (Dimenhydrinate); Cholinergics, e.g., Bethanechol, Oxotremorine, Methacholine, Cevimeline, Carbachol, Galantamine, Arecoline, Levaminsole; Acetylcholinesteriase Inhibitors, e.g., Edrophonium, Neostigmine, Donepezil, Tacrine, Echothiophate, Diisopropylfluorophosphate, Demecarium, Pralidoxime, Galanthamine, Tetraethyl pyrophosphate, Parathoin, Malathion, Isoflurophate, Metrifonate, Physostigmine, Rivastigmine, Abenonium, acetylchol, Carbaryl acetylchol, Propoxur acetylchol, Aldicarb acetylchol, Muscarinics, Muscarine, Pilocarpine, Magnesium; Calcium channel blockers, e.g., amlodipine besylate, Norvasc, diltiazem hydrochloride Cardizem CD, Cardizem SR, Dilacor XR, Tiazac, felodipine Plendil, isradipine DynaCirc, DynaCirc CR, nicardipine Cardene SR, nifedipine Adalat CC, Procardia XL, nisoldipine Sular, verapamil hydrochloride Calan SR, Covera HS, Isoptin SR, Verelan; Sodium channel blockers, e.g., moricizine, propafenone, encainide, flecainide, Tocainide, mexiletine, Phenytoin, Lidocaine, Disopyramide, Quinidine, Procainamide; Glucocorticoid receptor blocker, e.g., (Mifepristone); Peripheral adrenergic inhibitors, e.g., guanadrel Hylorel, guanethidine, monosulfate Ismelin, reserpine Serpasil, Mecamylamine, Hexemethonium; Blood vessel dilators, e.g., hydralazine hydrocholoride Apresoline, minoxidil Loniten; Central agonists, e.g., alpha methyldopa Aldomet, clonidine hydrochloride Catapres, guanabenz, acetate Wytensin, guanfacine hydrochloride Tenex; Combined alpha and beta blockers, e.g., labetolol hydrochloride, Normodyne, Trandate, carvedilol Coreg; Alpha blockers, e.g., doxazosin mesylate Cardura, prazosin hydrochloride Minipress, terazosin, hydrochloride Hytrin; Combination diuretics, e.g., amiloride hydrochloride+hydrochlorothiazide Moduretic, spironolactone+hydrochlorothiazide Aldactazide, triamterene+hydrochlorothiazide Dyazide, Maxzide; Potassium-sparing diuretics, e.g., amiloride hydrochloride Midamar, spironolactone Aldactone, triamterene Dyrenium; Nitrate pathway modulators, e.g., L-arginine, Nitroglycerin Deponit, Minitran, Nitropar, Nitrocine, Nitro Disc, Nitro-Dur, Nitrogard, Nitroglycerin, Nitroglycerin T/R, Nitro-Time, Nitrol ointment, Nitrolingual Spray, Nitrong, Nitro-Bid, Nitropress, Nitroprex, Nitro S.A., Nitrospan, Nitrostat, Nitro-Trans System, Nitro-Transdermal, Nitro-Time, Transderm-Nitro, Tridil. Pentaerythrito, I Tetranitrate, Peritrate, Peritrate S.A, Erythrityl, Tetranitrate, Cardilate, Isosrbide Dinitrate/Phenobarbital Isordil w/PB Isosorbide, Mononitrate, Imdur, ISMO, Isosorbide, Mononitrate, Monoket, Isosorbide, Nitrate; Cyclic nucleotide monophosphodiesterase (PDE) inhibitors; e.g., Levitra (vardenafil), Cialis (tadalafil), Viagra (sildenafil); Vasopressin inhibitors, e.g., atosiban, Alcohol, Relaxin; Renin inhibitors; e.g., Aliskiren; Estrogen and estrogen analogues and estrogen metabolites; Vesicular monoamine transport (VMAT) inhibitors; e.g., reserpine, tetrabenazine, Melatonin, Melatonin Analogues, 6-chloromelatonin, 2,3, dihydromelatonin, 6-chloro-2,3-dihydromelatonin, N-acetyl-N2-formyl-5-methoxy, kynurenamine, N-acetyl-5-methoxy kynurenamine; Progestrone inhibitors, e.g., ru486; Testosterone inhibitors, e.g., Spironolactone, cyproterone acetate; Gonadotropin-releasing hormone inhibitors, e.g., Leuprolide Acetate; Oxytocin inhibitors, e.g., Terbutaline Ritodrine, Glucagon Like Peptide 1; Dipeptidyl Peptidase IV inhibitors, e.g., LAF237 (novartis), P93/01 and P32/98 (Probiodrug AB), valine pyrrolidide (Novo Nordisk), dhea, adiponectin, phenserine, phosphodiesterase 4 inhibitor, valproate; Anticoagulants, e.g., Exanta (ximelagatran)—, Bilivarudin (hirulog), abciximab (Reopro®), Aggrenox® (dipridamole/ASA), anagrelide (Agrylin®), clopidogrel (Plavix), dipyridamole (Persantine®), tifabatide (Integrelin), ticlopidine (Ticlid®), tirofiban (aggrastat), ardeparin (Normiflo), Dalteparin (Fragmin), Danaparoid (Orgaran), Enoxaparin (lovenox), lepirudin (Refludan), Heparin, Warfarin; Thrombolytics, e.g., alteplase (Activase®, t-PA), reteplase (Retevase), Streptokinase, Urokinase; Other anticoagulants, e.g., aminocaproic acid (Amicar®), cilostazol (Pletal), erythropoietin (Epogen), filgrastim (G-CSF, Neupogen®), oprelvekin (Neumega), pentoxifylline (Trental); hmg1 antagonist; botox; and the like.

Pro sympathetic agents of interest include, but are not limited to: Beta-agonists, e.g., dobutamine, terbutaline, ritodrine, albuterol, metaproterenol; Alpha-1 agonists, e.g., phenylephrine, metaraminol, methoxamine; Prednisone & steroids; Indirect agents that include, but are not limited to, NE, ephedrine, phenylpropanolamine, cyclopentamine, tuaminoheptane, naphazoline, ampthetamine, tetrahydrozoline; Epinephrine/norepinephrine, Acetylcholine, Sodium, Calcium, ACE, Angiotensin, Aldosterone, Aldosterone Analogues, Fludrocortisone, 18-oxocortisol, deoxycorticosterone pivalate (DOCP) (ciba-geigy animal health); Potassium or magnesium channel blockers, e.g., valproate lithium, Cocaine; Amphetamines, e.g., Ephedrine, Terbutaline, Dopamine, Bromocriptine (Parlodel), Levodopa/Carbidopa, Dobutamine; Acupuncture; Adh vasopressin; Oxytocin pitocin; THC cannabinoids; Progesterone; Leptin; Galanin like peptide In certain embodiments, the pharmacologic agent that is administered as a symptom enhancement stimulus is not an inverse agonist as defined in publication nos. WO 2005/034871 and WO 2005/035731, such that it is not a substance that has an affinity for the inactive state of a receptor and thereby stabilizes the inactive state of the receptor, or a substance, including, but not limited to, drugs, hormones, or neurotransmitters, that produces inactivation of receptors and/or prevents or hinders activation by agonists, thereby reducing signaling from those receptors. In certain embodiments, the agent is not nadolol, bupranolol, butoxamine, carazolol, carvedilol, ICI-118, 551, levobunolol, metoprolol, propranolol, sotalol, and timolol, and the salts, solvates, analogues, congeners, bioisosteres, hydrolysis products, metabolites, precursors, and prodrugs thereof. In certain embodiments, the agent is not a "pressor" agent, such that it does not increase blood pressure.

Depending on the particular agent(s) administered to a subject, the agent(s) may be administered to a subject using a convenient delivery vehicle. Thus, a pharmacological agent may be incorporated into a variety of formulations for administration to a subject. A pharmacological agent may be formulated into pharmaceutical compositions by combination with appropriate, pharmaceutically acceptable carriers. By "pharmaceutically acceptable carrier" is meant a component such as a carrier, diluent, excipient, and the like of a composition that is compatible with the one or more pharmacological agents and other optional ingredients of the subject pharmacological agent compositions in that a pharmaceutically acceptable carrier may be combined with the pharmacological agent(s) without eliminating the biological or therapeutically effective activity of the one or more pharmacological agents, and is suitable for use in subjects as provided herein without undue adverse side effects (such as toxicity, irritation, allergic response, and death). Side effects are "undue" when their risk outweighs the benefit provided by the pharmaceutical agent. Non-limiting examples of pharmaceutically acceptable components include, but are not limited to, any of the standard pharmaceutical carriers such as phosphate buffered saline solutions, water, emulsions such as oil/water emulsions or water/oil emulsions, micro-emulsions, and various types of wetting agents. Accordingly, the pharmacological agents employed in the subject methods may be formulated into preparations in solid, semi-solid (e.g., gel), liquid or gaseous forms, such as tablets, capsules, powders, granules, ointments, solutions, suppositories, injections, inhalants and aerosols. As such, administration of a pharmacological agent may be achieved in various ways, including, but not limited to, oral, buccal (e.g. sub-lingual), rectal, topical (including both skin and mucosal surfaces, including airway surfaces), parenteral (e.g., subcutaneous, intramuscular, intradermal, intravenous and intrathecal), intraperitoneal, transdermal, intracheal, intravaginal, endocervical, intrathecal, intranasal, intravesicular, in or on the eye, in the ear canal, etc., administration. In certain embodiments, one or more pharmacological agents may be administered via a transdermal patch or film system such as or analogous to that described, e.g., in U.S. Pat. Nos. 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; and 4,585,452, the disclosures of which are herein incorporated by reference.

Embodiments may include pharmacological agent formulations for oral administration that may be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use may be obtained through combination of at least one pharmacological agent with a solid excipient, optionally grinding a resulting mixture, and processing the mixture of granules, after adding suitable additional compounds, if desired, to obtain tablets or dragee cores. Suitable solid excipients include, but are not limited to, carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethyl-cellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate; with optional lubricants, such as talc or magnesium stearate; and if desired, with diluents, buffering agents, moistening agents, preservatives and flavoring agents.

Accordingly, pharmacological agent formulations suitable for oral administration in accordance with the subject invention may be present in discrete units, such as capsules, cachets, lozenges, tablets, and the like, each containing a predetermined amount of the active pharmacological agent; as a powder or granules; as a solution or a suspension in an aqueous or non-aqueous liquid; or as an oil-in-water or water-in-oil emulsion. Such pharmacological agent formulations may be prepared by any suitable method of pharmacy which includes, but is not limited to, bringing into association the active pharmacological agent and a suitable carrier (which may contain one or more optional ingredients as noted above). For example, pharmacological agent formulations for use with the subject invention may be prepared by uniformly and intimately admixing the active pharmacological agent(s) with a liquid or finely divided solid carrier, or both, and then, if necessary, shaping the resulting mixture. For example, a tablet may be prepared by compressing or molding a powder or granules containing the active pharmacological agent, optionally with one or more accessory ingredients. Compressed tablets may be prepared by compressing, in a suitable machine, the pharmacological agent in a free-flowing form, such as a powder or granules optionally mixed with a binder, lubricant, inert diluent, and/or surface active/dispersing agent(s). Molded tablets may be made by molding, in a suitable machine, the powdered pharmacological agent moistened with an inert liquid binder.

Pharmacological agents may also be administered in the form of suppositories for rectal administration of the drug. These formulations may be prepared by mixing a pharmacological agent with a suitable non-irritating vehicle or excipient which is solid at ordinary temperatures but liquid at the rectal temperatures and will therefore melt in the rectum to release the drug. Such materials include, but are not limited to, cocoa butter, carbowaxes and polyethylene glycols. Embodiments include one or more pharmacological agent(s) made into suppositories by mixing with a variety of bases such as emulsifying bases or water-soluble bases. Pharmacological agents may also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

For example, embodiments may also include at least one pharmacological agent in an aerosolized, atomized or nebulized vapor form, e.g., administrable via a metered dose device or nebulizer, and the like such that embodiments also include aerosolizing, vaporing or nebulizing one or more pharmacological agents for administration to a subject. Accordingly, the one or more pharmacological agent agents may be utilized in aerosol formulation or an analogous formulation to be administered via inhalation or analogous means. The one or more pharmacological agents employed in the practice of the present invention may be formulated into pressurized acceptable propellants such as dichlorodifluoromethane, propane, nitrogen and the like.

Pharmacological agents may be delivered transdermally, by a topical route, formulated as applicator sticks, solutions, suspensions, emulsions, gels, creams, ointments, pastes, jellies, paints, powders, and aerosols. For example, embodiments may include a pharmacological agent formulation in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agent(s) are retained. The base or matrix layer may be operatively associated with a support or backing. Pharmacological agent formulations suitable for transdermal administration may also be delivered by iontophoresis and may take the form of an optionally buffered aqueous solution of the pharmacological agent compound. Suitable formulations may include citrate or bis/tris buffer (pH 6) or ethanol/water and contain a suitable amount of active ingredient.

Pharmacological agents may be provided as a salt and may be formed with one or more acids, including but not limited to hydrochloric, sulfuric, acetic, lactic, tartaric, malic, succinic, etc. Salts tend to be more soluble in aqueous or other protonic solvents that are the corresponding free base forms. In other cases, a preparation may be a lyophilized powder that is combined with buffer prior to use.

Pharmacological agents may be administered parenterally, such as intravenous (IV) administration, and may include a solution of the pharmacological agent dissolved in a pharmaceutically acceptable carrier. Among the acceptable vehicles and solvents that may be employed, include, but are not limited to, water and Ringer's solution, an isotonic sodium chloride, etc. In addition, sterile fixed oils may conventionally be employed as a solvent or suspending medium. For this purpose any bland fixed oil may be employed including synthetic mono- or diglycerides. In addition, fatty acids such as oleic acid can likewise be used in the preparation of injectables. Accordingly, a pharmacological agent may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of pharmacological agent in these formulations may vary widely, and will be selected based on fluid volumes, viscosities, body weight, and the like, in accordance with the particular mode of administration selected and the patient's needs. For IV administration, the formulation may be a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a nontoxic parenterally-acceptable diluent or solvent, such as a solution of 1,3-butanediol, and the like. Accordingly, pharmacological agent formulations suitable for parenteral administration may include sterile aqueous and non-aqueous injection solutions of one or more active pharmacological agents, which preparations may be isotonic with the blood of the intended recipient. These preparations may contain, buffers and solutes which render the formulation isotonic with the blood of the intended recipient. Aqueous and non-aqueous sterile suspensions may include suspending agents and thickening agents. The formulations may be presented in single- or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind described above.

Pharmacological agents may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the pharmacological agent into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). Accordingly, embodiments may include one or more pharmacological agents administered as liposomal formulations of the pharmacological agents. Methods for preparing liposomal suspensions are known in the art and thus will not be described herein in great detail. Briefly, in those embodiments where the pharmacological agent is an aqueous-soluble pharmacological agent, the pharmacological agent may be incorporated into lipid vesicles using conventional liposome technology. In such instances, due to the water solubility of the pharmacological agent, the pharmacological agent may be substantially entrained within the hydrophilic center or core of the liposomes. The lipid layer employed may be of any conventional composition and may either contain cholesterol or may be cholesterol-free. When the pharmacological agent of interest is water-insoluble, the pharmacological agent may be substantially entrained within the hydrophobic lipid bilayer which forms the structure of the liposome employing conventional liposome formation technology. In either instance, the liposomes which may be produced may be reduced in size, as through the use of standard sonication and homogenization techniques. Embodiments of liposomal formulations containing the pharmacological agent of interest may be lyophilized to produce a lyophilizate which may be reconstituted with a pharmaceutically acceptable carrier, such as water, to regenerate a liposomal suspension.

A pharmaceutical composition of the subject invention may optionally contain, in addition to a pharmacological agent, at least one other therapeutic agent useful in the treatment of a condition. Such other compounds may be of any class of drug or pharmaceutical agent, including but not limited to antibiotics, anti-parasitic agents, antifungal agents, anti-viral agents, anti-tumor agents, anti-neurodegenerative agents and anti-psychotic agents. When administered with anti-parasitic, anti-bacterial, anti-fungal, anti-tumor, anti-viral agents, anti-neurodegenerative, and anti-psychotic agents and the like, pharmacological agents may be administered by any method and route of administration suitable to the treatment of the condition, typically as pharmaceutical compositions.

Pharmacological agents may include compositions that may be prepared from water-insoluble compounds, or salts thereof, such as aqueous base emulsions. In such embodiments, the pharmacological agent composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

As noted above, in addition to active pharmacological agents, the compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Furthermore, pharmacological agent compositions may, though not always, contain microbial preservatives. Microbial preservatives that may be employed include, but are not limited to, methylparaben, propylparaben, and benzyl alcohol. The microbial preservative may be employed when the pharmacological agent formulation is placed in a vial designed for multi-dose use. Pharmacological agent compositions for use in practicing the subject methods may be lyophilized using techniques well known in the art.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Embodiments may also include administration of at least one pharmacological agent using a pharmacological delivery device such as, but not limited to, pumps (implantable or external devices), epidural injectors, syringes or other injection apparatus, catheter and/or reservoir operatively associated with a catheter, etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert at least one pharmacological agent into the delivery device for administration of the pharmacological agent to a subject and include, but are not limited to, vials, ampules, tubes, capsules, bottles, syringes and bags.

In certain embodiments, a pharmaceutically acceptable carrier may be preservative free. By "preservative free" is meant the substantial absence of chemical, antibacterial, antimicrobial, or antioxidative additives, or the like, from the pharmaceutically acceptable carriers of the present invention. "Substantial absence" may mean that no preservative is present in the compositions or that trace amounts may be present that impart no detectable effect otherwise attributable to a preservative. For example, the pharmaceutically acceptable carrier may be characterized by the substantial absence of chemical, antibacterial, antimicrobial, or antioxidative additives or the like (e.g., contain less than about 5.0, 4.0, 3.0, 2.0, 1.0, 0.5, 0.1, 0.05, 0.01, or even about 0.00 percent by weight of a preservative). Further, such formulations may be substantially or essentially free of alcohols such as ethanol (e.g., contain less than about 5.0, 4.0, 3.0, 2.0, 1.0, 0.5, 0.1, 0.05, 0.01, or even about 0.00 percent by weight of alcohols such as ethanol). Examples of suitable pharmacological agent formulations include, but are not limited to, formulations that include one or more active pharmacological agents and physiological saline solution (optionally including other typical ingredients such as other active agents and buffers).

As noted above, in pharmaceutical dosage forms, agents may be administered alone or with an appropriate association, as well as in combination, with other pharmaceutically active compounds. As used herein, "administered with" means that at least one pharmacological agent and at least one other adjuvant (including one or more other pharmacological agents) are administered at times sufficiently close that the results observed are indistinguishable from those achieved when one pharmacological agent and at least one other adjuvant (including one or more other pharmacological agents) are administered at the same point in time. The pharmacological agent and at least one other adjuvant may be administered simultaneously (i.e., concurrently) or sequentially. Simultaneous administration may be carried out by mixing at least one pharmacological agent and at least one other adjuvant prior to administration, or by administering the pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that at least one pharmacological agent and at least one other adjuvant are administered at the same point in time or immediately following one another. In the latter case, the at least one pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Unit dosage forms for oral or rectal administration such as syrups, elixirs, and suspensions may be provided wherein each dosage unit, for example, teaspoonful, tablespoonful, tablet or suppository, contains a predetermined amount of a pharmacological agent. Similarly, unit dosage forms for injection or intravenous or other suitable administration route may include the pharmacological agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of pharmacological agent calculated in an amount sufficient to produce the desired effect in association with a pharmaceutically acceptable diluent, carrier or vehicle. The specifications for the unit dosage forms of pharmacological agents of the present invention depend on, for example, the particular pharmacological agent(s) employed and the effect to be achieved, the pharmacodynamics associated with the particular pharmacological agent (s) in the subject, etc.

In certain embodiments, pharmaceutical agent delivery devices may be employed, such as body-associated, e.g., wearable, delivery devices, e.g., devices configured for application to a topical location or implantable devices. Such devices include implantable delivery devices, such as but not limited to those described in U.S. Pat. No. 8,303,536, the disclosure of which is herein incorporated by reference, and iontophoretic devices, such as but not limited to those described in U.S. Pat. Nos. 9,533,142; 9,327,114; 8,903,485; 8,190,252, the disclosures of which are herein incorporated by reference.

Embodiments include administering an effective amount of a first agent and an effective amount of a second agent. For example, embodiments may include administering a first agent and a second agent to provide an enhanced therapeutic effect. By "enhanced therapeutic effect" is meant that at least the desired outcome occurs more quickly and/or is of greater magnitude with a combination of the pharmacological agents, as compared to the same doses of each component given alone; or that doses of one or all component(s) are below what would otherwise be a minimum effective dose (a "sub-MED").

Any two pharmacological agents may be given in close enough temporal proximity to allow their individual therapeutic effects to overlap. For example, embodiments of the subject invention include the co-timely administration of a first and second agent, where "co-timely" is meant administration of a second pharmacological agent while a first pharmacological agent is still present in a subject in a therapeutically effective amount. It is to be understood that in some instances this will require sequential administration. Alternatively, multiple routes of administration may be employed, e.g., intravenous or subcutaneous injection combined with oral administration, and the like.

Embodiments also include pharmaceutical compositions in unit dosage forms that are useful which contain more than one type of pharmacological agent. In other words, a single agent administration entity may include two or more pharmacological agents. For example, a single tablet, capsule, dragee, trocheem suppository, syringe, and the like, combining two or more pharmacological agents would be a unit dosage form. The therapeutic agents present in a unit dosage form may be present in amounts such that, upon administration of one or more unit doses of the composition, a subject experiences, e.g., a longer lasting efficacy than with the administration of either agent alone and/or greater magnitude and/or quicker lowering of action. Such compositions may be included as part of a therapeutic package in which one or more unit doses are placed in a finished pharmaceutical container. Labeling may be included to provide directions for using the composition according to the invention. The actual amounts of each agent in such single unit dosage forms may vary according to the specific compositions being utilized, the particular compositions formulated, the mode of application, the particular route of administration, and the like, where dosages for a given subject may be determined using conventional considerations, e.g., by customary comparison of the differential activities of the subject compositions and of a known agent, or by means of an appropriate, conventional pharmacological protocol.

In some instances, a pharmaceutical composition that includes opposing pharmacological agents, such as first and second pharmacological agents having opposing physiological activity, e.g., a symptom enhancing pharmacological agent and a symptom diminishing pharmacological agent (e.g., a pro-parasympathetic agent, such as a beta blocker, and a pro-sympathetic agent, such as a beta-agonist), is administered to a subject during practice of the methods. In these embodiments, a single unit dosage of a pharmaceutical composition includes at least two pharmacological agents having opposing activity, where the composition may include more than one type of each pharmacological agent, e.g., may include two more of a first type of pharmacological agent having a first activity, e.g., symptom enhancing activity, and two or more pharmacological agents having a second type of activity, e.g., a symptom diminishing activity.

In some instances, a given pharmaceutical composition having two or more pharmacological agents of opposing activity, e.g., as described above, is configured to sequentially release the two or more pharmacological agents from the composition to the subject. For example, a pharmacological composition having a first symptom enhancing pharmacological agent and a second symptom diminishing pharmacological agent may be configured to release the symptom enhancing pharmacological agent prior to, i.e., before, the symptom diminishing pharmacological agent. In other embodiments, a pharmacological composition having a first symptom enhancing pharmacological agent and a second symptom diminishing pharmacological agent may be configured to release the symptom enhancing pharmacological agent after i.e., following, the symptom diminishing pharmacological agent. In such instances, any convenient formulation approach for providing sequential release of pharmaceutical active agents may be employed. For example, controlled release formulations that include one or more release modulating materials may be employed. For example, a given formulation may include a core that includes the second pharmacological agent surrounded by a delayed release shell which is, in turn, surrounded by an outer layer that includes the first pharmacological agent. Alternatively, a composition may be formulated where only the second pharmacological agent is encased in a delayed release coating material. Any convenient configuration that provides for differential, including fully sequential, release of the different active agents from the composition may be employed, as desired.

Examples of compositions configured to provide sequential delivery of opposing agents in accordance with embodiments of the invention include, but are not limited to, the following. In some embodiments, multi-particulate formulations may be employed. For example, pellets containing first or second active agents form the basis for sequential release of the active agents to a patient in need. The formulation will contain at least two populations of pellets, wherein at least one population comprises an immediate release population and at least one population comprises a delayed release population. The immediate release pellets release the first active agent immediately in the GI tract, whereas the modified release pellets release the second active agent at a later time inside the GI tract. The modified release pellets may be coated with either a pH dependent (enteric) coating or a time dependent coating so as to delay the second release of second active agent to the desired position in the GI tract. The pellets may be drug-layered pellets or matrix-type pellets. Also of interest are drug coated spheres/pellet with inert core formulations, wherein the formulation contains at least two populations of spheres/pellets with an inert core, wherein at least one population comprises an immediate release population and at least one population comprises a modified (i.e. sustained and/or delayed) release population. The immediate spheres/pellets with an inert core release the first active agent immediately in the GI tract, wherein the modified release spheres/pellets with an inert core release the second active agent at a later time inside the GI tract. The modified release spheres/pellets with an inert core may be coated with either a pH dependent (enteric) coating or a time dependent coating so as to delay release of the second active agent to the desired position in the GI tract. Also of interest are bi-layer tablets, where a tablet having both an immediate release layer and a modified release layer is employed. The immediate layer releases the first active agent immediately in the GI tract, whereas the modified release layer releases the second active agent at a later time inside the GI tract. The modified release layer may be coated with either a pH dependent (enteric) coating or a time dependent coating so as to delay release of the second active agent to the desired position in the GI tract. Also of interest are matrix tablets, e.g., that contain a well-mixed composite of drug(s) with rate-controlling excipients. Numerous sustained and/or delayed release tablets such as membrane controlled system, matrices with water soluble/insoluble polymers, and osmotic systems may be utilized. The delayed/sustained release can be achieved by applying a permeable or semipermeable membrane to the tablet core or by mixing the drug with excipient that is either a hydrophilic polymer with high viscosity and gel forming capability or a hydrophobic excipient that slows down the diffusion of drug molecule. An immediate release drug layer can be coated to the tablet that will be available for an early release in the GI tract, while the delayed release core will be designed to delay the drug release after a time period in a designed region of the GI tract. Also of interest are multicore tablets, e.g., that include discrete cores having at least one immediate release core and at least one delayed/sustained release core contained within the same tablet. The at least one immediate release core will be available for an early release in the GI tract, while the at least one delayed/sustained release core will be designed to delay the drug release after a time period in a designed region of the GI tract. Also of interest are gastroretentive delivery systems e.g., that contain a tablet or capsule having both an immediate release and modified release component. The immediate layer will release the first active agent immediately in the GI tract, wherein the modified release layer will release the second active agent at a later time inside the GI tract. The gastroretentive oral dosage form may utilize mucoadhesive, swellable, high density or floating technologies to prolong residence time in the stomach thereby allowing a prolonged period for release of both first and second releases in the stomach or upper GI.

The compositions of the present application may take the form of pulsatile delivery systems such as, for example, PULSINCAP®, MICROPUMP®, MEDUSA™, PORT® system, CHRONOTROPIC®, TIME CLOCK®, multilayered tablets, DiffuCORE®, rupturable tablets, ACCU-BREAK® system, DIFFUCAPS®, DIFFUTABS®, Eurand MINITABS®, MICROCAPS®, SODAS®, IPDAS®, OsDrC®, OptiDose®, OptiMelt™, ZYDIS®, CODAS®, PRODAS®, TMDS®, DMDS®, PMDS®, GEOCLOCK®, GEOMATRIX®, PULSYS®, OROS®, INTELLIMATRIX™ and VERSETROL™. Further details regarding multiple release formulations, materials that find use in such formulations and methods of fabricating the same may be found in United States Published Patent Application No. 20160158176, the disclosure of which is herein incorporated by reference.

Applying Electrical Energy

As noted above, certain embodiments include employing electrical modulation, in a manner effective to cause the desired symptom enhancement and/or diminishment according to the subject methods.

Any suitable area may be targeted for electrical modulation. Areas that may be targeted include, but are not limited to, pre- and post-ganglionic nerve fibers, as well as ganglionic structures, efferent and afferent nerve fibers, synapses, etc., and combinations thereof in certain embodiments. In certain embodiments, activity in a given nerve fiber may be electrically modulated in more than one area of the nerve fiber. In certain embodiments, electrical energy is applied to modulate synaptic efficiency, e.g., to increase or decrease the sensitivity of a synapse and include modulating presynaptic neurons.

As such, areas which may be targeted with electrical energy include, but are not limited to, pre- and post ganglionic nerve fibers, ganglionic structures, efferent and afferent nerve fibers, the hypothalamus, receptors any receptor described herein, afferent autonomic nerves (sympathetic and parasympathetic). Embodiments include receptors of the hypothalamus, including hormonal receptors on the hypothalamus. In certain embodiments, a given nerve fiber or the like may be targeted for electrical modulation in more than one area of the nerve fiber. Targeted areas of the nervous system which may be targeted in accordance with the subject invention include, but are not limited to, vagus nerve, optic ganglion, and sphenopalatine ganglion, internal carotid nerve and plexus, middle and superior cervical sympathetic ganglion; vertebral ganglion; cervicothoracic ganglion; sympathetic trunk; cervical cardiac nerves; cardiac plexus; thoracic aortic plexus; celiac ganglion; celiac trunk and plexus; superior mesenteric ganglion; superior mesenteric artery and plexus; intermesenteric plexus; inferior mesenteric ganglion; inferior mesenteric artery and plexus; superior hypogastric plexus; hypogastric nerves; vesical plexus; thoracic cardiac nerves; sympathetic trunk; 6th thoracic sympathetic ganglion; gray and white rami communicantes; greater, lesser and least splanchnic nerves; aorticorenal ganglion; lumbar splanchnic nerves; gray rami communicantes and sacral splanchnic nerves; and the like, or a combination of two or more of the above.

A number of different devices may be employed in accordance with the subject invention. For example, device and systems for applying electrical energy to a subject and which may be adapted for use in the subject invention are described, e.g., in U.S. Pat. Nos. 7,149,574 and 7,363,076, the disclosures of which are herein incorporated by reference. Such devices may be positioned directly on a targeted area, e.g., positioned below the skin of a subject directly on or adjacent a portion of the nervous system (e.g., one or more nerve fibers) such as an implantable device, or may be an external device (i.e., some or all of the device may be external to the subject). Such devices may be referred to as body-associated electrical stimulation devices, and may be topically located or implanted. In accordance with the subject invention, one or more electrodes or electrical contacts may be positioned directly on or adjacent a targeted area, where the one or more electrodes may be surgically implanted, e.g., directly on or adjacent a targeted nerve fiber of a subject. In certain embodiments, an immunomodulator such as a steroid or the like, may be incorporated into a surface contacting area of a device, e.g., to minimize inflammation of the targeted site.

An electric energy-applying device typically includes a stimulator such as an electrode, a controller or programmer and one or more connectors for connecting the stimulating device to the controller. In certain embodiments more than one electrode may be employed. In further describing representative electrodes, such are described in the singular, but it will be apparent that more than one electrode may be used, where such may be the same or may be different in one or more aspects. Accordingly, the description of an exemplary electrode suitable for use in the subject methods is applicable to other electrodes that may be employed.

The electrode employed in the subject invention is controllable to provide output signals that may be varied in voltage, frequency, pulse width, current and intensity. The electrode may be one that provides both positive and negative current flow from the electrode and/or may be capable of stopping current flow from the electrode and/or changing the direction of current flow from the electrode. For example, embodiments include an electrode that is controllable in these respects, i.e., controllable in regards to producing positive and negative current flow from the electrode, stop current flow from the electrode, change direction of current flow from the electrode, and the like. In certain embodiments, the electrode has the capacity for variable output, linear output and short pulse width.

The energy source for the electrical output may be provided by a battery or generator, such as a pulse generator, which battery or generator is operatively connected to the electrode. The energy source may be positioned in any suitable location such as adjacent to the electrode (e.g., implanted adjacent the electrode), or a remote site in or on the subject's body or away from the subject's body in a remote location and the electrode may then be connected to the remotely positioned energy source using wires, e.g., may be implanted at a site remote from the electrode or positioned outside the subject's body in certain instances. Of interest are implantable generators analogous to a cardiac pacemaker.

The electrode may be mono-polar, bipolar or multi-polar. In order to minimize the risk of an immune response triggered by the subject against the device and minimize damage such as corrosion and the like to the device from other biological fluids, etc., the electrode and any wires and optional housing materials are made of inert materials such as for example silicon, metal, plastic and the like. For example, a multi-polar electrode having about four exposed contacts (e.g., cylindrical contacts may be employed).

A controller or programmer may also be coupled with an electric energy-applying device. The programmer is typically one or more microprocessors under the control of a suitable software program. Other components of the programmer will be apparent to those of skill in the art, e.g., analog to digital converter, etc. The electric energy-applying device may be pre-programmed for desired parameters. In certain embodiments the parameters are controllable such that the electrode signal may be remotely modulated to desired settings without removal of the electrode from its targeted position. Remote control may be performed, e.g., using conventional telemetry with an implanted electric signal generator and battery, an implanted radiofrequency receiver coupled to an external transmitter, and the like. In certain embodiments, some or all parameters of the electrode may be controllable by the subject, e.g., without supervision by a physician. For example, a magnetic signal may be employed. In such embodiments, one or more magnets may be employed such that upon bringing a magnet in proximity to or away from the power source such as a pulse generator, the magnet may be employed to interfere with the electronic circuitry thus modulating the power—either increasing or decreasing the power supplied depending on whether the magnet is brought in proximity or moved away from the power source.

FIG. 1 shows an exemplary embodiment of an electric energy-applying device 100. Device 100 may be implanted in a suitable position of a subject's body 10. One or more leads 23 are shown positioned to provide stimulatory or inhibitory electrical energy. Device 100 include energy source 14 which may take the form of a modified signal generator, Model 7424 manufactured by Medtronic, Inc. under the trademark Intrel II. Lead 23 may take the form of any suitable lead, such as any of the leads that are sold with the Model 7427 and is coupled to energy source 14 by one or more conventional conductors 16 and 18. Lead 23 may include a paddle lead, a lead having one or more electrodes and/or catheters, or a combination catheter/lead capable of providing electrical impulses and pharmacological delivery. In certain embodiments, a lead may be composed of concentric tubes such as made of platinum or other like material. The tubes may be coated with a polymer except for the distal portions that may serve as the electrodes. Conductive wires carrying energy to the electrodes may be in the interior of the concentric tubes. Optionally, a distal electrode end may include a small recording microelectrode to help assist in the actual placement of the lead.

The present invention may be operated as an open-loop controlled system. In an open-loop system, the physician or patient may at any time manually or by the use of pumps or motorized elements adjust treatment parameters such as pulse amplitude, pulse width, pulse frequency, or duty cycle. Optionally, the present invention may incorporate a closed-loop control system which may automatically adjust the electrical parameters in response to a sensed parameter or condition of a subject. Under a closed-loop feedback system to provide automatic adjustment of parameters of the electrodes, a sensor that senses a condition of the body is utilized. More detailed descriptions of sensors that may be employed in the practice of the subject invention, and other examples of sensors and feedback control techniques that may be employed are disclosed in U.S. Pat. No. 5,716,377, which is incorporated herein by reference.

As shown in FIG. 1, the distal end of lead 23 terminates in one or more delivery elements such as stimulation electrodes which may be implanted using conventional surgical techniques. The type of treatment that is desired determines the location of the electrodes. Any number of electrodes may be used for various applications. Each of the electrodes may be individually connected to energy source 14 through lead 23 and conductors 16 and 18. Lead 23 may be surgically implanted either by a laminotomy or by a needle.

Energy source or signal generator 14 may be programmed to provide a predetermined stimulation (or inhibition) dosage in terms of pulse amplitude, pulse width, pulse frequency, or duty cycle. As shown, a programmer 20 may be utilized to provide stimulation (or inhibition) parameters to the delivery device via any suitable technology, e.g., using telemetry and the like. For example, in using telemetry, programmer 20 may be coupled to an antenna 24 via conductor 22. In certain embodiments, the programmer may be positioned, e.g., implanted, inside body 10. For example, in certain embodiments the programmer may be integrated with the energy source, electrode, etc., for example as a single unit.

Device 100 may optionally include one or more sensors to provide closed-loop feedback control of the treatment and/or electrode positioning. One or more sensors (not shown) may be attached to or implanted into a portion of a subject's body suitable for detecting a physical and/or chemical indicator of the subject. For example, sensing feedback may be accomplished, e.g., by a mechanical measure within a lead or an ultrasound or other sensor to provide information about the treatment parameters, lead positioning, LTP, etc.

Operative placement of a suitable electric energy applying device may be accomplished using any suitable technique. An electrode introducer needle may be employed to implant the electrode on or proximate to the area of interest. The size of the introducer needle may vary depending on the diameter of the electrode, etc., where in certain embodiments the electrode introducer needle may be a 12-gauge, 14-gauge, 16-gauge, 18-gauge, 20-gauge needle or 22-gauge needle, e.g., an electrode introducer needle available from Radionics in the Sluyter-Mehta kit as SMK 100 mm 2 mm active tip cannula. However, it should be understood that other electrode introducer needles may be used as appropriate to the needs and skill level of the practitioner performing the surgical procedure.

At least one imaging apparatus such as a CT scan, MRI apparatus, ultrasound apparatus, fluoroscope, or the like, may be employed to monitor the surgical. For exemplary purposes only, the subject method will be described using a fluoroscope, where such is in no way intended to limit the scope of the invention. The subject is placed in a suitable position for access e.g., supine, on a fluoroscopy table, with the patient's nose pointing vertically. The fluoroscope is then adjusted to a straight lateral position. And the entry point for the insertion of the electrode is determined.

Once the entry point is determined, the skin overlying the entry point is shaved and prepared with antiseptic solution. A 25-gauge needle may be used to inject a subcutaneous local anesthetic (such as, for example, 2 cc of 2% lidocaine) into the skin and subcutaneous tissues overlying the entry point. In addition to the local anesthetic, the patient may be given intravenous sedation and prophylactic antibiotics prior to commencement of the implantation procedure if desired.

The electrode introducer needle is inserted at the entry point and advanced. The fluoroscope may be adjusted as the needle is advanced. Once the needle is positioned the stylet is withdrawn from the electrode introducer needle. Once the implanted electrode is in place, the end of the electrode that is outside the skin is carefully held in place against the skin. The electrode introducer needle may then be slowly removed, leaving the implanted electrode in place. At this point, if desired, a few small subcutaneous sutures may be placed around the electrode to hold it in the desired position.

Once the needle has been completely removed and the implanted electrode is in the final position, then the proximal part of the electrode that is coming out of the skin may be secured to the skin of the subject, e.g., by adhesive tape. Additionally, a small incision may be made on the skin at the area the electrode exits the face. Then several subcutaneous sutures may be placed around the electrode to hold it in place. The distal end of the electrode may then be connected to an extension wire or catheter, which is tunneled to the subclavicular area, or another region which will house the device used as an energy source for the implanted electrode. The device or devices used to control the electrode may be surgically implanted in the desired region by procedures known in the art, such as have been applied in surgical neuromodulation therapies used to treat Parkinson's disease.

In certain embodiments of the subject invention, an electrode may be utilized which, instead of or in addition to delivering electric impulses to at least a portion of the autonomic nervous system, delivers a pharmacological agent to at least a portion of the autonomic nervous system. For example, an electrode may be used that has a small port at its tip which is connected to a reservoir or pump containing a pharmacological agent. The pharmacological agent delivery electrode may be implanted using an analogous procedure as that described above for the autonomic system modulating-electrode. In certain embodiments the reservoir or pump may also be implanted in the subject's body, analogous to that described above for the electrical impulse generator. The pharmacological agent delivery electrode may be controllable such that the amount of pharmacological agent delivered, the rate at which the pharmacological agent may be delivered, and the time period over which the pharmacological agent is delivered may be adjusted.

In embodiments in which electrical energy is used, any suitable protocol may be used, where certain protocols include using an electric energy-applying device to deliver a suitable amount of electrical energy to a subject. Once an electric energy-applying device is positioned in a suitable position on or about one or more targeted areas electrical energy is applied thereto for a period of time sufficient to provide the desired effect. This period of time will vary depending on the area (e.g., the nerve fiber) being treated, the condition being treated, etc. Certain embodiments include simultaneously monitoring (i.e., in "real time") the aspect of the nervous system such that a given nerve fiber may be electrically stimulated (or electrically inhibited) until the desired result is observed. Still further, in many embodiments once the desired result is achieved, a targeted area may be repeatedly electrically stimulated (or inhibited) one or more times to maintain the desired state such that the subject methods may be repeated one or more times, i.e., the subject methods include chronically applying electrical energy to a subject, such as chronically applying electrical energy to one or more nerve fibers. For example, in certain embodiments electrical stimulation (e.g., intermittent mild electrical pulses) may be delivered to a given area of the nervous system, twenty-four hours a day for a period of days, weeks, months, or even years in certain embodiments.

During the period of time that electrical energy is applied to a given area, the electrical energy may be substantially continuous, including continuous or intermittent (i.e., pulsed or periodic), where in many embodiments the electrical energy is in the form of electrical pulses. In other words, in certain embodiments electrical energy may be given continuously during the above-described period of time and in certain embodiments electrical energy may be given to an area in a pulsed or intermittent manner during the period of time described above. In accordance with the subject methods to apply electrical energy to a subject, once operatively positioned the electric energy applying device is activated to provide an electrical signal to the targeted area in a manner effective to practice the subject methods.

In practicing the subject methods, activation of the electric energy-applying device directly applies the electrical output of the device, i.e., electrical impulses, to the targeted area. The exact parameters of the applied electrical energy may vary depending on the particular subject, condition being treated, etc. For example, an electronic current wave may be provided when the electrical energy is applied. In certain embodiments, the current wave includes current waves of high frequency, e.g., high frequency pulses, where the current wave may also include low frequency amplitude modulation. In certain embodiments, a plurality of high frequency bursts of current pulses may be applied in addition to the application of underlying low frequency continuous stimulus. Stimulation may be monopolar or multipolar.

For example, to stimulate a targeted area, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 1 Hz to about 1000 Hz, e.g., from about 2 Hz to about 100 Hz in certain embodiments. In certain embodiments a pure d-c voltages may be employed. The pulse width may range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds. The electrical output may be applied for at least about 1 millisecond or more, e.g., about 1 second, e.g., about several seconds, where in certain embodiments the stimulation may be applied for as long as about 1 minute or more, e.g., about several minutes or more, e.g., about 30 minutes or more may be used in certain embodiments.

In certain embodiments, a control feedback loop is provided. For example, during or following a particular electric energy applying protocol, a biological aspect of a subject may be monitored, e.g., by sensing conduction in a neuronal system, e.g., in a particular electrically stimulated nerve fiber, or by any suitable method. For example, a sensor suitable for detecting nerve cell or axon activity may be implanted in a portion of a subject's body. A sensor may take the form of an electrode or the like. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. In utilizing a feedback system, if a predetermined detection criteria is not detected the same or a different stimulus protocol may be performed and may be automatically initiated under the control of a controller. For example, in those instances where a different protocol is performed, one or more of the electrical energy applying parameters may be modified, e.g., the pulse width may be increased, or the like, in the second protocol.

Behavioral Therapy

In some embodiments, the therapy that is administered to the subject is a behavioral therapy. By "behavioral therapy" is meant a protocol or regimen that results in a change in the behavior, i.e., the way that the subject acts, in a manner sufficient to modulate the dynamic measure of homeostatic capacity and treat the subject for the target condition. Behavioral therapies that may be employed may vary, where examples of such therapies include, but are not limited to: exercise regimens (e.g., cardiovascular, weight lifting, stretching, yoga); resting/sleeping regimens (e.g., meditation); physical therapies; psychological therapies, e.g., counseling for enhancement of emotions/mood; substance abuse therapies, e.g., smoking cessation therapies, alcohol abstinence therapies; drugs of abuse abstinence therapies, etc. Behavioral therapies may vary in terms of application, where examples include but are not limited to those that are administered via professional and/or consumer devices/services, e.g., mobile apps, videos, computers, etc.

Dietary Therapy

In some embodiments, the therapy that is administered to the subject is a dietary therapy. By "dietary therapy" is meant a protocol or regimen that results in a change in the nutritional and/or chemical intake of the subject, e.g., the types of foods/liquids that the subject ingests or otherwise introduces into the body, in a manner sufficient to modulate the dynamic measure of homeostatic capacity and treat the subject for the target condition. Dietary therapies that may be employed may vary, where examples of such therapies include, but are not limited to: low carbohydrate diets, low fat diets, low calorie diets, vegetarian diets, organic diets, etc.; nutritional supplement regimens, e.g., vitamin regimens; etc.

Environmental Therapy

In some embodiments, the therapy that is administered to the subject is an environmental therapy. By "environmental therapy" is meant a protocol or regimen that results in a change in the contextual environment of the subject, e.g., the perceived surroundings of the subject, in a manner sufficient to modulate the dynamic measure of homeostatic capacity and treat the subject for the target condition. Environmental therapies that may be employed may vary, where examples of such therapies include, but are not limited to: changes in day/night duration; changes in geographic locations, e.g., to obtain a desired temperature and/or elevation, etc.

Increasing Homeostatic Capacity

In some embodiments, administration of opposing stimuli in accordance with the methods, e.g., as described above, results in increasing a subject's homeostatic capacity. As such, methods of increasing a subject's homeostatic capacity, i.e., enhancing the homeostatic capacity of a subject, are provided. Homeostasis refers to the tendency of biological systems to maintain relatively constant conditions in the internal environment while continuously interacting with and adjusting to changes originating within or outside the system. Homeostasis involves continuous motion, adaptation, and change in response to environmental factors. It is through homeostatic mechanisms that body temperature is kept within normal range, the osmotic pressure of the blood and its hydrogen ion concentration (pH) is kept within strict limits, nutrients are supplied to cells as needed, and waste products are removed before they accumulate and reach toxic levels of concentration. These are but a few examples of the thousands of homeostatic control systems within the body. Some of these systems operate within the cell and others operate within an aggregate of cells (organs) to control the complex interrelationships among the various organs. Homeostatic capacity refers to the capability of systems, such as described above, to self-stabilize in response to stressors.

By enhancing homeostatic capacity in a subject is meant at least increasing the homeostatic capacity of the subject by a measurable amount, e.g., as determined using the protocol described below. For example, the methods may include at least partially restoring the homeostatic capacity of the subject. By "at least partially restoring the homeostatic capacity of the subject" is meant that the homeostatic capacity of the subject is enhanced or improved, e.g., to that of a target value, which target value may be a "normal" value or greater than a normal value, e.g., a super-normal value. By "normal" is meant the homeostatic capacity of a healthy subject of a particular age. In certain embodiments, the healthy subject is a healthy human at an age after puberty, e.g., 18 year old, 19 year old, 20 year old, 21 year old, 22 year old, 23 year old, 24 year old, 25 year old, 26 year old, 27 year old, 28 year old, 29 year old, 30 year old, 31 year old, 32 year old, 33 year old 34 year old, 35 year old, 36 year old, 37 year old, 38 year old, 39 year old, 40 year old, 41 year old, 42 year old, 43 year old, 44 year old, 45 year old, 46 year old, 47 year old, 48 year old, 49 year old or 50 year old. In some instances, the normal function with respect to homeostatic capacity is that of a healthy human 25 year old. By super normal value is meant the homeostatic capacity of a subject having greater than normal homeostatic capacity, e.g., that of an athlete, etc. The magnitude of difference between normal and super normal may vary, and in some instances may be 5% or greater, such as 10% or greater, including 15%, 20% or 25% or greater, where in some instances the target super normal homeostatic capacity is 5% to 75% greater than of a normal homeostatic capacity. In some instances, the methods include enhancing the homeostatic capacity of the subject to that which is at least closer to a target homeostatic capacity. By "at least closer" is meant, in some instances, that the target homeostatic capacity is restored to be 50% or more, e.g., 75% or more of the target function, such as 80% or more of the target function, including 90% or more of the target function, e.g., 95% or more of the target function, including 99% or more of the target function.

In some embodiments, the homeostatic capacity of the subject is enhanced, e.g., as described above, by increasing the dynamic range of target homeostatic system or component thereof of the subject. Target homeostatic systems include, but are not limited to: sub-cellular systems, cellular systems, supra-cellular, e.g., organ systems, etc. Homeostatic systems may further be described functionally. Examples of homeostatic systems of interest include, but are not limited to: circadian rhythm systems, e.g., master circadian rhythm control (i.e., master clock system), peripheral circadian rhythm systems (i.e., peripheral oscillator system), thermoregulatory control systems, blood pressure control (i.e., regulatory) systems, osmoregulation control (i.e., regulatory) systems, pH control (i.e., regulatory) systems, glucose concentration control systems, calcium regulation control systems, body fluid control systems, etc. The target homeostatic system component may be any part (i.e., unit or element) of a homeostatic system, e.g., as described above.

In some instances, the target homeostatic system component is an organ or component thereof, e.g., a portion of the organ. Organs if interest include, but are not limited to: cardiovascular system organs, e.g., heart, blood and blood vessels; digestive system organs, e.g., salivary glands, esophagus, stomach, liver, gallbladder, pancreas, intestines, colon, rectum and anus; endocrine system organs, e.g., hypothalamus, pituitary gland, pineal body or pineal gland, thyroid, parathyroids and adrenals, i.e., adrenal glands; excretory system organs, e.g., kidneys, ureters, bladder and urethra; lymphatic system organs, e.g., tonsils, adenoids, thymus and spleen; integumentary system organs, e.g., skin, hair and nails; muscular system organs, e.g., muscles; nervous system organs, e.g., brain, spinal cord and nerves; reproductive system organs, e.g., the sex organs, such as ovaries, fallopian tubes, uterus, vagina, mammary glands, testes, vas deferens, seminal vesicles, prostate and penis; respiratory system organs, e.g., pharynx, larynx, trachea, bronchi, lungs and diaphragm; skeletal system organs, e.g., bones, cartilage, ligaments and tendons. In some instances, the component is a cell or component thereof, e.g., an organelle, such as mitochondria, endoplasmic reticulum, flagellum, golgi apparatus, vacuole and nucleus.

Embodiments of the methods may further include evaluating homeostatic capacity of a subject. As reviewed above, homeostatic capacity refers to the ability of a subject to maintain relatively constant conditions in the internal environment while continuously interacting with and adjusting to changes originating within or outside the system. By "evaluating" is meant assessing, analyzing or assaying to provide a form of measurement, e.g., in the form of a determination or proxy thereof, of the homeostatic capacity of the subject. The evaluations that may be made may be quantitative and/or qualitative determinations, and be represented as a value or set of values, as desired.

Aspects of the methods of certain embodiments include obtaining dynamic biometric data from a subject. The phrase "biometric data" is employed to refer to a measure of a biometric parameter that relates to the physiology of a living organism, e.g., as described below. As such, the biometric parameter which is employed in methods of the invention to obtain the biometric data may be a parameter that provides information about an organism's vital functions, including growth and development, the absorption and processing of nutrients, the synthesis and distribution of proteins and other organic molecules, the functioning of different tissues, organs, and other anatomic structures; the psychological and/or behavioral state of the subject, e.g., mental and/or cognitive state of the subject, which may be subjective or objective, self-reported or third party observed, as desired; etc.

Biometric parameters that are measured may vary widely, where examples of such parameters include physiological, chemical, electrical, behavioral, psychological, etc., based parameters, as well as variations and derivatives thereof. Biometric parameters of interest include, but are not limited to: physical parameters, e.g., blood pressure, orthostatic hypotension, pulse pressure, heart rate, heart rate variability (HRV), heart rate recovery, resting heart rate, respiration rate, forced expiratory volume, forced vital capacity, temperature, core temperature, galvanic skin response, gastro-intestinal motility, sleep cycle, VO2 max, bone density, weight, body mass index (BMI), bone density, waist to hip ratio, waist circumference, other obesity measures (e.g., volume displacement, Dual Energy X-ray Absorptiometry (i.e., DEXA), etc.), baroreceptor sensitivity, oxygen saturation, nervous system activity measurements, including electrical potential measurements, such as spontaneous electrical potential measurements, e.g., EEG, EMG EKG, evoked electrical potential measurements, e.g., sensory evoked potentials (such as auditory invoked potentials (e.g., brain stem evoked response or potential (ABER or ABEP), visual evoked potentials, tactile or somatosensory evoked potentials, laser evoked potentials), motor evoked potentials, etc.; nerve conduction measures, e.g., motor NCS, sensory NCS, F-wave study, H-reflex study, spf-NCS, etc.; and the like, and combinations thereof; sample analysis obtainable parameters, e.g., pH level, cortisol level, ACTH level, Epinephrine/Norepinephrine level, oxygen saturation, insulin, glucose, inflammatory/immune markers, DNA methylation, DNA double strand breaks, clock genes/factors, oxidative stress, telomere status, gut biome, melatonin level, adenosine level, creatinine, urea nitrogen, c-reactive protein, hemoglobin, triglycerides, lipoproteins, apolipoprotein B100/A1 ratio, white blood cell count, cholesterol, oxygen saturation, and the like, and combinations thereof. Dynamic biometric data may be made up of information about a single type of biometric parameter, or two or more different types of biometric parameters. The biometric data employed in methods of the invention may thus be made up of information obtained by measuring or assessing one or more biometric parameters, such as the ones listed above.

As summarized above, the biometric data that is obtained and employed in embodiments of the invention is dynamic biometric data. By "dynamic biometric data" is meant biometric data that incorporates some type of change component, as opposed to static biometric data. The change component may vary widely, where examples of change components include, but are not limited to components that are: temporal and/or in response to an applied stimulus and/or in response to withdrawal of stimulus and/or in response to a change in the contextual environment of the subject. For example, the dynamic biometric data that is obtained may be biometric data obtained over a given period of time. The given period of time may vary, ranging in some instances from 0.1 seconds to 24 hours, such as 1 second to 12 hours, e.g., 1 second to 1 hour, including 1 second to 1 minute. Where the dynamic biometric data is data obtained over a given period of time, the data may be obtained continuously over that period of time or at one or more distinct points during that period of time. For example, the biometric parameter(s) that is monitored in order to obtain biometric data may be monitored continuously during the given period of time, i.e., it may be obtained in an uninterrupted manner, i.e., without cessation, during the given period of time. Alternatively, the biometric parameter(s) that is monitored in order to obtain biometric data may be monitored intermittently during the given period of time, i.e., it may be obtained at one or more points over the given period of time, with an interval between points at which it is not obtained. In some embodiments, the interval may vary, ranging, for example, from 0.01 sec to 60 minutes or longer, such as 0.1 to 60 s. In some instances, the dynamic biometric data is obtained by evaluating a biometric parameter for a rate of change over a period of time. As such, methods may include obtaining information about the speed at which a biometric parameter of interest changes over a given period of period of time. Obtaining dynamic biometric data as described above provides for numerous benefits, including increases in temporal resolution, as compared to single point in time data. Dynamic biometric data as obtained herein provides a truer and more meaningful measure of the biometric value(s) of interest, as compared to single point in time measurements.

Dynamic biometric data of interest also include biometric data that is obtained by evaluating a biometric parameter for a change in response to an applied stimulus. Such biometric data may include data that is obtained before and/or after application of the stimulus to the subject. In some instances, the biometric data may be obtained over a given period of time that spans or follows the application of the stimulus to the subject. This type of biometric data may be viewed as biometric data that is obtained over a given period of time in conjunction with application of a stimulus to the subject being evaluated. The applied stimulus may vary, where stimuli of interest include physical stimuli and chemical stimuli. Physical stimuli of interest include, but are not limited to, change in orientation of the subject, exercise, change in temperature experienced by the subject or a portion thereof, and the like. Chemical stimuli of interest include, but are not limited to, administration of various active agents, e.g., orally, topically, by injection or other type of administration route, where active agents of interest include, but are not limited to: sugars, starches, stimulants, and the like.

Dynamic biometric data of interest also include biometric data that is obtained by evaluating a biometric parameter for a change in response to withdrawal of a stimulus. Such biometric data may include data that is obtained before and/or after withdrawal (e.g., blockage) of the stimulus to the subject. In some instances, the biometric data may be obtained over a given period of time that spans or follows the withdrawal of the stimulus to the subject. This type of biometric data may be viewed as biometric data that is obtained over a given period of time in conjunction with withdrawal of a stimulus to the subject being evaluated. The withdrawn stimulus may vary, where stimuli of interest include physical stimuli and chemical stimuli. Physical stimuli of interest include, but are not limited to, change in orientation of the subject, exercise, change in temperature experienced by the subject or a portion thereof, and the like. Chemical stimuli of interest include, but are not limited to, administration of various active agents, e.g., orally, topically, by injection or other type of administration route, where active agents of interest include, but are not limited to: sugars, starches, stimulants, and the like.

Dynamic biometric data of interest also include biometric data that is obtained by evaluating a biometric parameter for a change in response to modulation of the contextual environment of the subject. By contextual environment of the subject is meant the perceived environment of the subject. Such biometric data may include data that is obtained before and/or after the modulation in the contextual environment of the subject. In some instances, the biometric data may be obtained over a given period of time that spans or follows the modulation of the contextual environment of the subject. This type of biometric data may be viewed as biometric data that is obtained over a given period of time in conjunction with modulation of the contextual environment of the subject. The modulation of the contextual environment of the subject may vary, where contextual modulations of interest include, but are not limited to, change in day and night duration, change in temperature, change in humidity, change in elevation, change in atmosphere, and the like.

Dynamic biometric data of interest also include biometric data that is obtained by evaluating a biometric parameter for a change in response to modulation of the behavioral aspect of the subject. By behavioral aspect of the subject is meant an observable activity of the subject. Such biometric data may include data that is obtained before and/or after the modulation of the behavioral aspect of the subject. In some instances, the biometric data may be obtained over a given period of time that spans or follows the modulation of the behavioral aspect of the subject. This type of biometric data may be viewed as biometric data that is obtained over a given period of time in conjunction with modulation of the behavioral aspect of the subject. The modulation of the behavioral aspect of the subject may vary, where behavioral modulations of interest include, but are not limited to, dietary changes, sleep pattern changes, activity level changes, and the like.

As reviewed above, a variety of different biometric parameters may be measured to obtain the dynamic biometric data. The method by which the biometric data is obtained may vary depending on the nature of the biometric parameter that is monitored. In some instances, the method employed to obtain the biometric data includes physically monitoring the subject to obtain the dynamic biometric data. For example, physical monitoring of the subject may be employed where the biometric parameter is one or more of blood pressure, orthostatic hypotension, pulse pressure, heart rate, heart rate variability (HRV), heart rate recovery, resting heart rate, respiration rate, forced expiratory volume, forced vital capacity, temperature, core temperature, galvanic skin response, gastrointestinal motility, sleep cycle, VO2 max, bone density, weight, body mass index (BMI), bone density, waist to hip ratio, waist circumference, other obesity measures (e.g., volume displacement, Dual Energy X-ray Absorptiometry (i.e., DEXA), etc.), baroreceptor sensitivity, oxygen saturation, nervous system activity measurements, including electrical potential measurements, such as spontaneous electrical potential measurements, e.g., EEG, EMG EKG, evoked electrical potential measurements, e.g., sensory evoked potentials (such as auditory invoked potentials (e.g., brain stem evoked response or potential (ABER or ABEP), visual evoked potentials, tactile or somatosensory evoked potentials, laser evoked potentials), motor evoked potentials, etc.; brain activity, function and structure related biometric data, e.g., as captured by functional Magnetic Resonance Imaging (fMRI), magnetoencephalography (MEG) and electroencephalography (EEG); nerve conduction measures, e.g., motor NCS, sensory NCS, F-wave study, H-reflex study, spf-NCS, etc.; and combinations thereof. Any convenient protocol for physically monitoring a subject for one or more of the above biometric parameters may be employed, and methods for physically monitoring each are known in the art. For example, where the biometric parameter of interest is HRV, the physical monitoring may include measures such as low frequency peak ("LF"), high frequency peak ("HF"), and the LF/HF ratio to determine HRV and obtain the HRV derived biometric data. Other methods of obtaining biometric data of interest include, but are not limited to: retinal scan, photograph and video images; and the like.

In some embodiments, the dynamic biometric data is obtained by a method that includes analyzing a sample from the subject to obtain the dynamic biometric data. The sample that is analyzed may vary, where samples of interest include, but are not limited to: urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, and the like, and may employ conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like. Biometric parameters that may be monitored by evaluating a sample from the subject include, but are not limited to: pH level, cortisol level, ACTH level, Epinephrine/Norepinephrine level, oxygen saturation, insulin, glucose, inflammatory/immune markers, DNA methylation, DNA double strand breaks, clock genes/factors, oxidative stress, telomere status, gut biome, melatonin level, adenosine level, creatinine, urea nitrogen, c-reactive protein, hemoglobin, triglycerides, lipoproteins, apoloipoprotein B100/A1 ratio, white blood cell count, cholesterol, oxygen saturation, and combinations thereof.

Any convenient protocol for physically monitoring a subject for one or more of the above biometric parameters may be employed, and methods for testing a sample for monitoring each are known in the art. In some instances, the dynamic biometric data is obtained by both physically monitoring the subject and by assaying a sample from the subject, e.g., as described above.

Aspects of the methods further include evaluating the homeostatic capacity of the subject from the dynamic biometric data. As such, following obtainment of the dynamic biometric data, the homeostatic capacity of the subject is evaluated based on the obtained dynamic biometric data. Any convenient protocol may be employed to evaluate the homeostatic capacity of the subject based on the obtained dynamic biometric data. For example, the obtained dynamic biometric data may be compared to control or reference sets of dynamic biometric data to obtain the homeostatic capacity evaluation. In some instances, the obtained dynamic biometric data may be compared to a suitable database of control or reference sets to obtain the homeostatic capacity evaluation. The control or references sets of data may be made up of data obtained from multiple different individuals of known homeostatic capacity. The data may be made up from individuals of a variety of different ages and health, including from young and old individuals, as well as healthy and diseased individuals, as desired. Any suitable comparison algorithm may be employed, and the output homeostatic capacity evaluation may be produced in a variety of different formats or configurations. This homeostatic capacity evaluation step may be performed using a suitable functional module of a computing device/system, e.g., as described in greater detail below.

The homeostatic capacity evaluation that is provided by embodiments of the invention may vary, as desired. For example, the evaluation may be an output in the form of a qualitative assessment, e.g., bad, poor, average, good and exceptional, etc. The output may be in the form of a quantitative assessment, e.g., where the homeostatic capacity evaluation output a number selected from a numerical scale. The homeostatic capacity evaluation output may provide assessment with respect to a number of different homeostatic capacity parameters, such as but not limited to: the robustness, dynamic range, resilience, coping mechanism, anti-fragility, etc., of the homeostatic capacity of the individual. The output showing the homeostatic capacity of the animal/person may be provided as a proxy for the biological age (as opposed to the chronological age) of the subject, e.g., by using statistical correlations relative to the general population. For example, the homeostatic capacity evaluation produced from dynamic biometric data from a 50 year old professional cyclist in great condition could suggest that the "biological age" of that person based on homeostatic capacity measures is actually much younger, e.g., that of a 35 years old from the general population. In some instances, the homeostatic capacity evaluation is one that is prepared by comparing the obtained dynamic biometric data to a database that includes data comprising statistically meaningful values that correlate each biometric value and/or a combination of the biometric values of interest to the values of different ages or age ranges of cohorts for the same biometric value(s). For example, in instances where the obtained biometric data may be from an individual or animal that is 30 years of age, the homeostatic capacity evaluation may be performed by comparing the obtained biometric data to data obtained from healthy individuals from a variety of ages ranging from 20 to 80 years, and show a correlation to a certain age of the individual as a whole or certain systems thereof, e.g., cardiovascular system, neurological system, reproductive system, etc. For example, the output homeostatic capacity evaluating may be an overall composite number, e.g., that the individual has the homeostatic capacity of a 32 year old, or be more granular with respect to particular biological systems of the individual, e.g., where the output is that the system provides a homeostatic capacity evaluation in which the subject has a cardiovascular system of a 25 year old but the nervous system of a 35 year old. In such instances, these sub-categories could be at systems levels of the body and could be more granular, e.g., portions of systems.

In some instances, the methods may include use of one or more static measures of homeostatic capacity. Such measures may be used as separate measures, or composites of dynamic and static measurements may be employed.

Methods of assessing homeostatic capacity that may be employed in embodiments of the invention include those described in U.S. patent Ser. Nos. 15/061,645; 15/363,980 and 15/363,988; the disclosures of which are herein incorporated by reference.

Methods of Treating a Subject for a Condition

A variety of different conditions, such as disease condition, are treatable by the subject methods. In certain embodiments, the disease condition is one in which the body mounts a compensatory response to a symptom enhancing stimulus administered to suppress or decrease one or more symptoms of the disease. In other words, the disease condition is one that is characterized by the presence of a compensatory response to a symptom enhancing stimulus that reduces the magnitude of one or more symptoms of the disease. In certain embodiments, the disease condition is a condition that is characterized by the presence of a compensatory mechanism to a directly acting therapeutic approach.

In certain embodiments, the disease condition is a manifestation of an irregularity in a homeostatic pathway, and as such one that may be treated by enhancing homeostatic capacity in the subject, where such conditions included, but are not limited to, those described in U.S. patent application Ser. Nos. 15/363,988 and 15/363,980; the disclosures of which are herein incorporated by reference. In certain embodiments, the disease condition is manifested by chronic sympathetic bias. In certain embodiments, the disease condition is manifested by chronic vagal bias.

In certain embodiments, the disease condition is a cardiovascular disease. For example, short-term administration of adrenergic agonists may be employed in the treatment of hypertension, e.g., to achieve the desired short term increase or enhancement of sympathetic bias and concomitant long term decrease in sympathetic bias. In certain embodiments, the disease condition is a neurological condition. For example, short-term administration of a serotonin antagonist may be employed to treat depression, by causing a long-term compensatory response in the body in the form of increased serotonin receptor sensitivity. In certain embodiments, the disease condition is an immune condition. For example, a pro-inflammatory agent may be administered in short duration to treat asthma, where the short duration of pro-inflammatory agent cause the body to mount a compensatory response that results in decreased inflammation. In certain embodiments, the disease condition is an endocrine system condition. For example, in the treatment of diabetes, an insulin blocker may be administered on a short term basis, causing the body to mount a compensatory response, e.g., in the form of increased insulin receptor sensitivity. See the experimental section below for further discussion of these representative embodiments. In certain embodiments, the disease is not a pulmonary airway disease, e.g., asthma, emphysema or chronic obstructive pulmonary disease.

Utility

The subject methods find use in a variety of applications, as reviewed above. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. In certain embodiments, such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

As indicated above, the subject methods may be used in the treatment of a variety of different disease conditions, including, but not limited to: cardiovascular diseases, such as atherosclerosis, coronary artery disease, hypertension, hyperlipidemia, eclampsia, pre-eclampsia, cardiomyopathy, volume retention, congestive heart failure, QT interval prolongation, aortic dissection, aortic aneurysm, arterial aneurysm, arterial vasospasm, myocardial infarction, reperfusion syndrome, ischemia, sudden adult death syndrome, fatal arrhythmias, coronary syndromes, coronary vasospasm, sick sinus syndrome, bradycardia, tachycardia, arrhythmias, thromboembolic disease, deep vein thrombosis, coagulopathy, DIC, mesenteric ischemia, syncope, venous thrombosis, arterial thrombosis, malignant hypertension, secondary hypertension, primary pulmonary hypertension, secondary pulmonary hypertension, Raynaud's, paroxysmal supraventricular tachycardia, and the like; neurodegenerative diseases, such as Alzheimer's, Pick's, Parkinson's, amyotrophic lateral sclerosis, neuroinflammatory diseases, viral meningitis, viral encephalitis, fungal meningitis, fungal encephalitis, multiple sclerosis, charcot joint, schizophrenia, and the like; orthopedic inflammatory diseases, such as osteoarthritis, reflex sympathetic dystrophy, osteoporosis, regional idiopathic osteoporosis, Paget's disease, juvenile chronic arthritis, antigen-induced arthritis, and the like; inflammatory conditions, such as ARDS, multiple sclerosis, rheumatoid arthritis, migraines, chronic headaches, and the like; lymphoproliferative diseases, such as lymphoma, lymphoproliferative disease, Hodgkin's disease, inflammatory pseudotumor of the liver, and the like; autoimmune diseases, such as Graves disease, Hashimoto's, Takayasu's disease, Kawasaki's disease, arteritis, scleroderma, CREST syndrome, allergies, dermatitis, Henoch-Schlonlein purpura, goodpasture syndrome, autoimmune thyroiditis, myasthenia gravis, lupus, Reiter's syndrome and the like; inflammatory and infectious diseases, such as sepsis, diseases of wound healing, viral infections, wound healing, tuberculosis, infection, fungal infections, AIDS, human immunodeficiency virus and the like; pulmonary diseases, such as tachypnea, fibrotic lung diseases, cystic fibrosis, interstitial lung disease, desquamative interstitial pneumonitis, non-specific interstitial pneumonitis, lymphocytic interstitial pneumonitis, usual interstitial pneumonitis, idiopathic pulmonary fibrosis, pulmonary edema, aspiration, asphyxiation, pneumothorax, right-to-left shunts, left-to-right shunts, respiratory failure, and the like, gastrointestinal disorders, such as hepatitis, xerostomia, bowel mobility, constipation, irritable bowel syndrome, peptic ulcer disease, ileus, post-operative bowel dysmotility, inflammatory bowel disease, typhlitis, cholelethiasis, cholestasis, fecal incontinence, cyclic vomiting syndrome, diverticulitis/diverticulosis, and the like; endocrine disorders, such as hypothyroidism, diabetes, obesity, syndrome X, hyperglycemia, insulin resistance, PCOS, and the like; genitourinary disorders, such as bladder dysfunction, renal failure, erectile dysfunction, hyperreninemia, hepatorenal syndrome, pulmonary renal syndrome, incontinence, arousal disorders, menopausal mood disorders, premenstrual mood disorders, and the like; skin disorders, such as wrinkles, cutaneous vasculitis, and the like; aging associated diseases and conditions, such as shy dragers, multi-symptom atrophy, age related inflammation conditions, cancer, aging and the like; Th-2 dominant, such as diseases typhlitis, osteoporosis, lymphoma, myasthenia gravis, lupus and the like; conditions that cause hypoxia, hypercarbia, and/or acidosis, such as COPD, emphysema, any chronic lung disease that causes acidosis, sudden infant death syndrome, sudden adult death syndrome, acute pulmonary embolism, chronic pulmonary embolism, pleural effusion, cardiogenic pulmonary edema, non-cardiogenic pulmonary edema, acute respiratory distress syndrome ("ARDS"), neurogenic edema, acidosis of any causehypercapnia, acidemia, renal tubular acidosis, asthma, any chronic lung disease that causes hypoxia or hypercarbia or hypercapnia, and the like; Neurologic diseases, such as epilepsy, seizures, stroke, insomnia, sleep disorders, cerebral vascular accident, transient ischemic attacks, headaches, concussions, post-concussive syndrome, cerebral vascular, vasospasm, central sleep apnea, obstructive sleep apnea, stress, bipolar disorder, migraines, chronic headaches, ADEM, depression, and the like; pediatric conditions, e.g., respiratory distress syndrome, sudden infant death syndrome, Hirschsprung's disease, bronchopulmonary dysplasia, congenital megacolon, aganglionosis, juvenile rheumatoid arthritis, juvenile chronic arthritis and the like; OB-GYN diseases, e.g., amniotic fluid embolism, pregnancy-related arrhythmias, fetal stress, fetal hypoxia, amniotic fluid embolism, gestational diabetes, pre-term labor, cervical incompetence, fetal distress, peri-partum maternal mortality, labor complications, premenstrual syndrome, dysmenorrhea, endometriosis, and the like; as well as other conditions, including but not limited to: chronic pain, glaucoma, trauma, hospitalization, post-operative recovery, post-procedural recovery, transplant-related side effects, fibrosis, transplant-related tachycardia, transplant rejection, transplant-related bowel dysmotility, transplant-related hyperreninemia, male infertility, disorders of thermoregulation, fibromyalgia, and the like; menstrual related disorders, e.g., pelvic pain, dysmenorrhea, gi disease, nausea, etc.; peripartum and pregnancy related disorders; peripartum cardiomyopathy; sickle cell disease; reperfusion injury; central serous choroidoretinopathy; stress; post traumatic stress disorder; gulf war syndrome; etc.

Disease conditions and methods/devices for treating the same with symptom enhancement that may be treated according to embodiments of the invention that employ both symptom enhancement and symptom diminishment, e.g., as described above include, but are not limited to, those described in: U.S. Pat. Nos. 8,691,877; 8,788,041; and 8,571,650; the disclosures of which are herein incorporated by reference.

Devices and Systems

A number of different devices and systems may be employed in accordance with the subject invention, e.g., as described above. Devices and systems that may be adapted or configured for use in the subject invention include devices and systems for administering a therapeutic treatment regimen, e.g., such as described above, to a subject. In some instances, the devices and systems may further be configured for obtaining dynamic biometric data from a subject and optionally further processing the obtained data in some, e.g., in making a homeostatic capacity evaluation of the subject based on the obtained dynamic biometric data, in making a dynamic diagnosis based on the obtained dynamic biometric data, etc. In some instances, the devices may be configured to also output a therapeutic treatment regimen recommendation based on the homeostatic capacity evaluation.

Devices of interest may include one or more functional modules, which may be distributed among two or more distinct hardware units or integrated into a single hardware unit, e.g., as described in greater detail below. Devices/systems may include a therapeutic treatment module, which is configured to administer a therapy to a subject, such as electrical therapy, pharmacological therapy, etc., e.g., as described above, in accordance with methods of the invention. In certain embodiments, the module may control the device to administer a pharmacological agent to a subject, e.g., the module may be configured to administer a suitable dosage, etc. In certain embodiments the module may control a device to administer electrical energy to a subject, e.g., may control the activation/termination of electrical energy including selecting suitable electrical parameters. The module may be configured to, or otherwise be capable of, directing a microprocessor to activate, i.e., turn "on" and "off" an electric energy applying device for applying energy to a subject. For example, if so determined, the module may direct the electric energy applying device to provide the appropriate energy to result in the desired action. Accordingly, a module may select the appropriate parameters (e.g., frequency, amplitude, etc.) depending on what is required and direct an electric energy-applying device to implement the parameters.

In some instances, the devices include one or more of a dynamic biometric data obtainment module, a homeostatic capacity evaluation module, and a homeostatic capacity evaluation output module. The dynamic biometric obtainment module is adapted to obtain dynamic biometric data, e.g., by being in operational communication with one or more biometric parameter sensors and or an input configured to receive dynamic biometric data from a source of such data, and transmit the obtained biometric data to the process unit module. The homeostatic capacity evaluation module is adapted to retrieve the dynamic biometric data from the dynamic biometric data obtainment module and make a homeostatic capacity evaluation therefrom. As such, the module is configured to produce a homeostatic capacity evaluation from the received or input dynamic biometric data.

In some instances, the systems further include a therapeutic treatment regimen module, which is configured to identify a suitable therapeutic regimen based on the homeostatic capacity evaluation.

The output module, when present, is adapted to provide the homeostatic capacity evaluation (and in some instances a therapeutic treatment regimen) to a user, e.g., the subject or interested stakeholder. In some instances, the output module is configured to display the homeostatic capacity evaluation to a user, e.g., via graphical user interface (GUI). In one embodiment, a visual display can be used for displaying the homeostatic capacity evaluation. Other outputs may also be employed, e.g., printouts, messages (e.g., text messages or emails) sent to another display device, to a storage location for later viewing (e.g., the cloud), etc.

One embodiment of a device for evaluating a subject's homeostatic capacity is configured as follows. A dynamic biometric obtainment module is configured to obtain subject's dynamic biometric data. This biometric data from the subject may then be input into a homeostatic capacity evaluation module, along with biometric data from a database, which contains data made up from individuals of a variety of different ages and health of known homeostatic capacities. The homeostatic capacity evaluation module evaluates the subject's homeostatic capacity based on the biometric data from the subject and from the database using a classification rule derived from a machine learning algorithm, which may be any convenient algorithm, such as but not limited to: Fisher's linear discriminant, logistic regression, naïve Bayes classifier, quadratic classifiers, k-nearest neighbor, decision trees, neural networks, and support vector machine. The homeostatic capacity evaluation module may then output the subject's predicted homeostatic capacity in a user-readable format via a homeostatic capacity evaluation output module. Homeostatic capacity evaluation devices are further described in United States Published Patent Application Number 20160256108, the disclosure of which is herein incorporated by reference.

As would be recognized by one of skilled in the art, many different software, firmware, hardware options and data structures can be employed in devices of the invention, e.g., as described above. In some instances, a general-purpose computer can be configured as a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into a memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the datafiles and the programming can be exported to a cloud computer, which runs the program, and returns an output to the user.

The memory of a computer system can be any device that can store information for retrieval by a processor, and can include magnetic or optical devices, or solid-state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent (i.e., volatile) memory. A file in permanent memory can be editable and re-writable. Operation of the computer is controlled primarily by operating system, which is executed by a central processing unit. The operating system can be stored in a system memory. In some embodiments, the operating system includes a file system. In addition to the operating system, one possible implementation of the system memory includes a variety programming files and data files for implementing the method described above.

Where desired, the devices may include one or more sensors, e.g., configured to obtain biometric data, e.g., as described above. In certain aspects, a sensor includes one or more, such as a set of two or more, such as two or three, electrodes that provide for sensing. For example, the electrodes may be configured to generate electrocardiogram data. Alternatively, physiological sensors distinct from electrodes may be included in the device. For example, a temperature sensor, such as a thermistor, CMOS temperature sensor, resistive temperature devices (RTDs), may be employed to obtain precise measurements of temperature. An additional physiological sensor may include an LED and a photodiode combined into a pulse oximeter, which may be employed to measure blood oxygenation, which would also give information about pulse pressure. The device may also include analyte detection sensors. For example, specific chemical sensors may be incorporated into the devices to detect the presence of various agents, e.g., alcohol, glucose, BNP (B-type Natriuretic peptide, which is associated with cardiac disease), etc. Sensors of interest include those configured to detect the presence of a chemical analyte in a biological fluid sample, where analytes of interest include, but are not limited to: blood sugar (glucose), cholesterol, bilirubin, creatine, various metabolic enzymes, hemoglobin, heparin, hematocrit, vitamin K or other clotting factors, uric acid, carcinoembryonic antigen or other tumor antigens, various reproductive hormones such as those associated with ovulation or pregnancy, drugs of abuse and/or metabolites thereof; blood alcohol concentration, etc. In certain aspects, substances or properties for which the receiver is configured to detect include lactate (important for athletes), oxygen, pH, alcohol, tobacco metabolites, and illegal drugs (important for both medical diagnosis and law enforcement). Where the devices include an analyte detecting sensing element, this sensing element can be configured in the receiver in a number of different ways. For example, a sensor that includes a selectively permeable membrane which is permeable to the agent one wants to detect may be provided, where there is an isolated cell behind the membrane and the agent passes through the membrane. Changes in the properties, such as electrical properties, of the cell, are then measured. In certain aspects, a small reservoir on the side of the devices with a membrane across it is employed, and electrical circuitry behind it is measured. Also of interest are ChemFET sensors, which are based on the binding of analyte to the sensor causing a change in the conductivity. In certain aspects, a material whose electrical properties (or other properties) are changed when the material, e.g., protein analyte, binds to it are employed. Blood alcohol concentration may be determined any number of ways, including but not limited to: sensors that analyze fluid samples, such as perspiration, optical spectroscopic sensors, etc.

Of interest are receivers that include at least an electrocardiography (ECG) sensor module. An ECG sensor module is a module which is configured to obtain ECG data and, if desired, additionally perform one or more of processing the data in some way, storing the data and retransmitting the data. The ECG data may be employed by the receiver to derive a number of different metrics, including but not limited to: R-wave, heart rate, heart rate variability, respiration rate, etc. Where the device includes one or more physiological sensing functionalities, the device may further include sensing modules that are configured to obtain and process data from these sensing functionalities. For example, where the device includes an ECG sensing functionality, the device may include an appropriate functional module (for example in the form of programming) that can handle and process the raw data from these sensors.

In some instances, devices/systems as described herein include instructions for operating in a manner to apply a therapeutic regimen, e.g., as described above. In certain embodiments, instructions in accordance with the methods described herein can be coded onto a computer-readable medium in the form of "programming", where the term "computer readable medium" as used herein refers to any storage or transmission medium (including non-transitory version so such) that participates in providing instructions and/or data to a computer for execution and/or processing. Programming may take the form of any convenient algorithms. In some instances, programming may include, for example, discriminant analysis, classification analysis, cluster analysis, analysis of variance (ANOVA), regression analysis, regression trees, decision trees, nearest neighbor algorithms, principal components, factor analysis, ensemble learning, AdaBoost, ALOPEX, analogical modeling, cascading classifiers, case-based reasoning, classifier chains, co-training, information fuzzy networks, logic learning machine, perceptron, multidimensional scaling and other methods of dimensionality reduction, likelihood models, hypothesis testing, kernel density estimation and other smoothing techniques, cross-validation and other methods to guard against overfitting of the data, the bootstrap and other statistical resampling techniques, artificial intelligence, including artificial neural networks, machine learning, data mining, and boosting algorithms, and Bayesian analysis, etc.

Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer. The computer-implemented method described herein can be executed using programming that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

As mentioned above, the functional modules may be performed by a variety of different hardware, firmware and software configurations. In some instances, the functional modules will be distributed among a system of two or more distinct devices, e.g., mobile devices, remote devices (such as cloud server devices), laboratory instrument devices, etc., which may be in communication with each other, e.g., via wired or wireless communication. In other instances, the distinct functional modules will be integrated into a single device. Where the distinct functional modules are integrated into a single device, the device may have a variety of configurations. For example, the device may be a laboratory device, which may or may not be configured to a bench top device. In yet other instances, the device may be a handheld device, e.g., a smartphone or tablet type device. In yet other instances, the device may be a wearable device, such as a watch type device, a wearable patch type device, etc.

Embodiments of the invention may employ virtual reality components and virtual reality mediated protocols. Virtual reality (both display and input devices) or other such simulators may be employed. Virtual reality and similar simulators may be employed to collect data (e.g., through the use of various biometric sensors that work in conjunction with virtual reality systems, such as measuring heart rate, eye movements and blink rates, measuring electrical impulses on the head (e.g., ear, neck, etc.), brain waves, etc.). Virtual reality and similar simulators may be employed to apply various stimuli (e.g., create a psychological/physiological condition such as fear of heights, etc., and the attendant increases in blood pressure, psychological distress, etc.). Virtual reality and similar simulators may be employed in therapeutic embodiments, for example, to induce physiological, chemical, electrical, behavioral, and or psychological change—e.g., to overcome phobias, to reduce blood pressure/treat hypertension (e.g., via paradoxically elevating pressure), treat depression, improve mood and well-being, improve system balance or ability to restore balance, etc. In such instances, any convenient virtual reality input devices or similar simulators, incorporating one or more of the senses, may be employed, e.g., to improve homeostatic capacity at all system levels. Suitable virtual reality systems include consumer use at home, at retail locations (as a service), or medical grade, e.g., that are configured to be used in clinic settings or at home. Where desired, the virtual reality systems may be connected to other devices, such an exercise machine with various biometric monitors to collect data, apply stimuli and be used for therapy. These could be used for any number of medical indications, performance enhancement for athletes, general consumer wellness use, etc.

In addition, the present invention contemplates the storage and access to information present thereon, e.g., therapeutic administration, concerning treatment regimen, homeostatic capacity evaluation, etc., where such access may be public or via an appropriate secured and private setting, e.g., wherein HIPAA standards are followed, such that the system may be HIPAA compliant.

Kits

Also provided are kits for practicing the subject methods. Kits may include one or more components employed in a given method of the invention, such as but not limited to, pharmaceutical compositions, including pharmaceutical compositions that include pharmacological agents of opposing activity, pharmaceutical agent delivery devices, electric energy applying devices, etc., as described above.

In some instances, the subject kits include one or more pharmacological agents, as described above. The dosage amount of the one or more pharmacological agents provided in a kit may be sufficient for a single application or for multiple applications. Accordingly, in certain embodiments of the subject kits a single dosage amount of a pharmacological agent is present and in certain other embodiments multiple dosage amounts of a pharmacological agent may be present in a kit. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit is dictated by the particular pharmacological agent employed, as described above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperitoneal, intradermal, transdermal, intracheal, etc. Accordingly, certain systems may include a suppository applicator, syringe, I.V. bag and tubing, electrode, etc.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

The following examples are offered by way of illustration and not by way of limitation.

EXPERIMENTAL

I. Example of Opposing Pharmacologic Stimulation Therapy

An example of utilizing therapy for the treatment of hypertension includes using a short-acting sympathomimetic agent to produce short intervals of increased blood pressure ranging from seconds to hours and a short-acting parasympathomimetic agent to induce short intervals of decreased blood pressure ranging from seconds to hours to increase dynamic range and therefore homeostatic capacity of the subject, thereby treating the subject for hypertension. In addition, measured feedback to regulate the frequency and duration of pulsed therapies may be employed.

A. Dog Studies

Example Study 1: Effect of Opposing Pharmacologic Stimulation Therapy in Hypertensive Dogs Double-blinded randomized controlled studies are performed in a set of dogs with experimentally induced hypertension to demonstrate that intermittent stimulation with sympathomimetic and parasympathomimetic pharmacologic agents lowers blood pressure. Experiments are conducted on mongrel dogs of either sex weighing 14-17 kg. Dogs are prepared for study by being treated for ectoparasites and endoparasites in addition to being immunized for parvovirus, canine distemper, hepatitis, parainfluenza, and coronavirus. All experiments are conducted in accordance with the National Institutes of Health Guide for the Care and Use of Laboratory Animals. Dogs are fed a low sodium diet supplemented with sodium chloride to achieve a sodium intake of 40 mmol/d (normal sodium intake). This dietary regimen provides a constant and known level of dietary sodium intake. Throughout the experimental protocol, all dogs are allowed water ad libitum.

For implantation of catheters for controlled administration of the agents, dogs are anesthetized with sodium thiamylal (30 mg/kg IV) for induction and then halothane (1%). Catheters are inserted via the femoral vessels into the aorta for direct arterial pressure measurement and drug administration. All catheter lines are tunneled subcutaneously to the midscapular region of the back and exteriorized. A 10-day steady state control period precedes the experimental period for all subjects to allow for recovery from surgical instrumentation.

Throughout the experimental period, dogs in the treatment group receive dosages of a sympathomimetic at 8 AM every morning, followed by administration of dosages of a parasympathomimetic at 4 PM every afternoon. Dogs in the control group receive a placebo at the same frequency during the experimental period. Measurement of systolic, diastolic, and mean arterial blood pressures are obtained via pressure transducer on an ongoing basis. Measurements continue for a recovery period of 15 days following completion of pharmacologic administration.

All dogs in the treatment group are observed to initially have either no changes or statistically negligible increases in systolic, diastolic, and mean arterial pressures. At some point during the experimental period these dogs are observed to begin to manifest reductions in systolic, diastolic, and mean arterial pressures. The frequency and dosage of administration of opposing therapies is gradually adjusted so as to increase the magnitude of the reduction for the duration of the experimental period. These reductions are maintained upon cessation of the treatment for the duration of the recovery period. Evaluation of biometric data, e.g., as described in United States Published Application No. 20160256108, the disclosure of which is herein incorporated by reference, reveals an increase in homeostatic capacity. Dogs in the control group maintain the same values in these parameters throughout both the control period and the experimental period. No adverse effects of treatment are found in any of these subjects.

Example Study 2: Effect of Opposing Pharmacologic Stimulation Therapy Provided by a Single Combination Therapy Dosage in Hypertensive Dogs Double-blinded randomized controlled studies are performed in a set of dogs with experimentally induced hypertension to demonstrate that intermittent stimulation with sympathomimetic and parasympathomimetic pharmacologic agents lowers blood pressure. Experiments are conducted on mongrel dogs of either sex weighing 14-17 kg. Dogs are prepared for study by being treated for ectoparasites and endoparasites in addition to being immunized for parvovirus, canine distemper, hepatitis, parainfluenza, and coronavirus. All experiments are conducted in accordance with the National Institutes of Health Guide for the Care and Use of Laboratory Animals. Dogs are fed a low sodium diet supplemented with sodium chloride to achieve a sodium intake of 40 mmol/d (normal sodium intake). This dietary regimen provides a constant and known level of dietary sodium intake. Throughout the experimental protocol, all dogs are allowed water ad libitum.

Throughout the experimental period, at 8 AM every morning dogs in the treatment group receive an ingestible tablet dosage that includes a beta agonist with immediate release and a beta blocker with delayed release, such that drugs of opposite effect peak in out-of-phase fashion. The net effect is that the dogs experience drugs of opposing effects at different time points after administration. Dogs in the control group receive a placebo at the same frequency during the experimental period. Measurement of systolic, diastolic, and mean arterial blood pressures are obtained via pressure transducer on an ongoing basis. Measurements continue for a recovery period of 15 days following completion of pharmacologic administration.

All dogs in the treatment group are observed to initially have either no changes or statistically negligible increases in systolic, diastolic, and mean arterial pressures. At some point during the experimental period these dogs are observed to begin to manifest reductions in systolic, diastolic, and mean arterial pressures. The frequency and dosage of administration of opposing therapies is gradually adjusted so as to increase the magnitude of the reduction for the duration of the experimental period. These reductions are maintained upon cessation of the treatment for the duration of the recovery period. Evaluation of biometric data, e.g., as described in United States Published Application No. 20160256108, the disclosure of which is herein incorporated by reference, reveals an increase in homeostatic capacity. Dogs in the control group maintain the same values in these parameters throughout both the control period and the experimental period. No adverse effects of treatment are found in any of these subjects.

B. Human Studies

Example Study 1: Effect of Opposing Pharmacologic Stimulation Therapy in Hypertensive Patients Double-blinded randomized controlled studies are performed in a set of patients with essential hypertension to demonstrate that intermittent electrical stimulation of sympathetic nerves lowers blood pressure. In all patients, hypertension is confirmed on at least three occasions in an outpatient setting after the patient has been sitting for at least 10 minutes. Blood pressure ranges recorded indicate elevation of both systolic and diastolic components of the blood pressure. No patients have clinical signs or symptoms of pheochromocytoma or renal artery stenosis, and no patients have clinical or laboratory evidence of impaired cardiac, renal, pulmonary, or hepatic function. Urinalysis and serum concentrations of creatinine, sodium, and potassium are confirmed to be within normal limits for patients.

All medications are stopped for each individual for at least four weeks before the beginning of the study. All patients remain hospitalized throughout the study, where physical activity consists of only daily walks. Throughout the study, each patient ingests a constant amount of a nutritionally adequate whole-foods diet intrinsically low in sodium chloride (approximately 10 mmoles NaCl/70 kg body weight/day). A sodium chloride supplement is added in an amount sufficient to increase total sodium intake to 140 meq/day/70 kg. The diet provides approximately 55 mmoles of potassium, 375 mg of calcium, and 820 mg of phosphorus per 70 kg/day.

In each patient, the total number of calories provided is determined from the estimated amount of energy required to keep body weight constant. The diet contains, as a percentage of total calories, 35% fat, 56% carbohydrate, and 9% protein. The specific ingredients of each meal are kept constant throughout the study. Fluid intake is fixed at 3150 ml/70 kg/day.

A 10-day steady state control period precedes the experimental period for all subjects. Throughout the experimental period, all patients in the treatment group initially receive dosages of a sympathomimetic at 8 AM every morning, followed by administration of dosages of a parasympathomimetic at 4 PM every afternoon. Control subjects would have similar catheters implanted but receive only placebo for the duration of the treatment period.

Blood pressure is measured in the nondominant arm at 8 am, noon, 4 pm, 8 pm, and 10 pm of each day, with an automated oscillometric device (Dinamap) in order to avoid observer bias. At each measurement session, after the patient has been supine for 10 minutes, five measurements of systolic and diastolic pressure and heart rate are obtained and the average of the last four measurements are calculated. The measurements are repeated with the patient in the upright position at each session. The measurements are averaged to yield values for daily systolic and diastolic blood pressures. Mean arterial pressure is calculated as (systolic pressure−diastolic pressure)/3+diastolic pressure. Measurements continue for a recovery period of 15 days following completion of pulsed administration.

All patients in the treatment group initially have either no changes or statistically negligible increases in systolic, diastolic, and mean arterial pressures. At some point during the experimental period these patients begin to manifest reductions in systolic, diastolic, and mean arterial pressures. The frequency and dosage of administration is gradually adjusted so as to increase the magnitude of the reduction for the duration of the experimental period. These reductions are maintained upon cessation of the treatment for the duration of the recovery period. Evaluation of biometric data, e.g., as described in United States Published Application No. 20160256108, the disclosure of which is herein incorporated by reference, reveals an increase in homeostatic capacity. Patients in the control group maintain the same values in these parameters throughout both the control period and the experimental period. No adverse effects of treatment are found in any of these subjects.

Example Study 2: Effect of Opposing Pharmacologic Stimulation Therapy Provided by a Single Combination Therapy Dosage in Hypertensive Patients Double-blinded randomized controlled studies are performed in a set of patients with essential hypertension to demonstrate that intermittent electrical stimulation of sympathetic nerves lowers blood pressure. In all patients, hypertension is confirmed on at least three occasions in an outpatient setting after the patient has been sitting for at least 10 minutes. Blood pressure ranges recorded indicate elevation of both systolic and diastolic components of the blood pressure. No patients have clinical signs or symptoms of pheochromocytoma or renal artery stenosis, and no patients have clinical or laboratory evidence of impaired cardiac, renal, pulmonary, or hepatic function. Urinalysis and serum concentrations of creatinine, sodium, and potassium are confirmed to be within normal limits for patients.

All medications are stopped for each individual for at least four weeks before the beginning of the study. All patients remain hospitalized throughout the study, where physical activity consists of only daily walks. Throughout the study, each patient ingests a constant amount of a nutritionally adequate whole-foods diet intrinsically low in sodium chloride (approximately 10 mmoles NaCl/70 kg body weight/day). A sodium chloride supplement is added in an amount sufficient to increase total sodium intake to 140 meq/day/70 kg. The diet provides approximately 55 mmoles of potassium, 375 mg of calcium, and 820 mg of phosphorus per 70 kg/day.

In each patient, the total number of calories provided is determined from the estimated amount of energy required to keep body weight constant. The diet contains, as a percentage of total calories, 35% fat, 56% carbohydrate, and 9% protein. The specific ingredients of each meal are kept constant throughout the study. Fluid intake is fixed at 3150 ml/70 kg/day.

Throughout the experimental period, at 8 AM every morning patients in the treatment group receive an ingestible tablet dosage that includes a beta agonist with immediate release and a beta blocker with delayed release, such that drugs of opposite effect peak in out-of-phase fashion. The net effect is that the patients experience drugs of opposing effects at different time points after administration. Patients in the control group receive a placebo at the same frequency during the experimental period. Measurement of systolic, diastolic, and mean arterial blood pressures are obtained via pressure transducer on an ongoing basis. Measurements continue for a recovery period of 15 days following completion of pharmacologic administration.

Blood pressure is measured in the nondominant arm at 8 am, noon, 4 pm, 8 pm, and 10 pm of each day, with an automated oscillometric device (Dinamap) in order to avoid observer bias. At each measurement session, after the patient has been supine for 10 minutes, five measurements of systolic and diastolic pressure and heart rate are obtained and the average of the last four measurements are calculated. The measurements are repeated with the patient in the upright position at each session. The measurements are averaged to yield values for daily systolic and diastolic blood pressures. Mean arterial pressure is calculated as (systolic pressure−diastolic pressure)/3+diastolic pressure. Measurements continue for a recovery period of 15 days following completion of pulsed administration.

All patients in the treatment group initially have either no changes or statistically negligible increases in systolic, diastolic, and mean arterial pressures. At some point during the experimental period these patients begin to manifest reductions in systolic, diastolic, and mean arterial pressures. The frequency and dosage of administration is gradually adjusted so as to increase the magnitude of the reduction for the duration of the experimental period. These reductions are maintained upon cessation of the treatment for the duration of the recovery period. Evaluation of biometric data, e.g., as described in United States Published Application No. 20160256108, the disclosure of which is herein incorporated by reference, reveals an increase in homeostatic capacity. Patients in the control group maintain the same values in these parameters throughout both the control period and the experimental period. No adverse effects of treatment are found in any of these subjects.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a subject for a condition by increasing homeostatic capacity, the method comprising:
   (a) enhancing at least one symptom of the condition by applying a symptom enhancing stimulus to the subject, wherein the symptom enhancing stimulus is a pharmacological agent; and
   (b) diminishing the at least one symptom of the condition by applying a symptom diminishing stimulus to the subject, wherein the symptom diminishing stimulus is a different pharmacological agent with respect to the symptom enhancing stimulus;
   in a manner effective to increase homeostatic capacity and thereby treat the subject for the condition, wherein the symptom enhancing stimulus and the symptom diminishing stimulus have opposing physiological activity and the condition is hypertension.

2. The method according to claim 1, wherein the condition is a manifestation of an irregularity in a homeostatic pathway.

3. The method according to claim 1, wherein each of the symptom enhancing and diminishing is of limited temporal duration.

4. The method according to claim 1, wherein the method comprises administering a pharmaceutical composition that includes both a symptom enhancing pharmacological agent stimulus and a symptom diminishing pharmacological agent stimulus.

5. The method according to claim 4, wherein the pharmaceutical composition is formulated to sequentially release the symptom enhancing pharmacological agent stimulus and the symptom diminishing pharmacological agent stimulus.

6. The method according to claim 5, wherein the pharmaceutical composition is formulated to release the symptom enhancing pharmacological agent stimulus prior to the symptom diminishing pharmacological agent stimulus.

7. The method according to claim 5, wherein the pharmaceutical composition is formulated to release the symptom enhancing pharmacological agent stimulus after the symptom diminishing pharmacological agent stimulus.

8. The method according to claim 4, wherein the pharmaceutical composition comprises a beta agonist and a beta blocker.

9. The method according to claim 8, wherein the beta agonist is released prior to the beta blocker.

10. The method according to claim 1, wherein the method comprises monitoring the subject.

11. The method according to claim 1, wherein the method enhances the subject's homeostatic capacity by increasing the dynamic range of a homeostatic system response.

12. The method according to claim 1, wherein the opposing physiological activity comprises receptor agonism and receptor antagonism.

13. The method according to claim 1, wherein:
   the symptom enhancing stimulus comprises a pro-sympathetic agent; and
   the symptom diminishing stimulus comprises a pro-parasympathetic agent.

* * * * *

UNITED STATES PATENT AND TRADEMARK OFFICE
CERTIFICATE OF CORRECTION

PATENT NO. : 11,382,513 B2
APPLICATION NO. : 15/804336
DATED : July 12, 2022
INVENTOR(S) : Yun et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 184 days.

Signed and Sealed this
Eleventh Day of February, 2025

Coke Morgan Stewart
*Acting Director of the United States Patent and Trademark Office*